United States Patent
Hansson et al.

(10) Patent No.: US 12,251,293 B2
(45) Date of Patent: Mar. 18, 2025

(54) PROPHYLACTIC DRESSING

(71) Applicant: Mölnlycke Health Care AB, Gothenburg (SE)

(72) Inventors: Dennis Hansson, Gunnilse (SE); Karin Glasmästar, Hisings Backa (SE); Anna Grou, Gothenburg (SE); Conny Jakobsson, Lerum (SE); Océane Lançon, Säve (SE)

(73) Assignee: Mölnlycke Health Care AB, Mölndal (SE)

( * ) Notice: Subject to any disclaimer, the term of this patent is extended or adjusted under 35 U.S.C. 154(b) by 149 days.

(21) Appl. No.: 16/770,148

(22) PCT Filed: Dec. 12, 2018

(86) PCT No.: PCT/EP2018/084627
§ 371 (c)(1),
(2) Date: Jun. 5, 2020

(87) PCT Pub. No.: WO2019/115645
PCT Pub. Date: Jun. 20, 2019

(65) Prior Publication Data
US 2020/0383836 A1 Dec. 10, 2020

(30) Foreign Application Priority Data

Dec. 15, 2017 (EP) ..................... 17207749
Dec. 15, 2017 (EP) ..................... 17207759

(51) Int. Cl.
*A61F 13/0203* (2024.01)
*A61F 5/34* (2006.01)
(Continued)

(52) U.S. Cl.
CPC ............ *A61F 13/0213* (2013.01); *A61F 5/34* (2013.01); *A61F 13/0226* (2013.01);
(Continued)

(58) Field of Classification Search
CPC .. A61F 13/02; A61F 13/0203; A61F 13/0206; A61F 13/0213; A61F 13/0216;
(Continued)

(56) References Cited

U.S. PATENT DOCUMENTS 4,727,868 A * 3/1988 Szycher .............. A61F 13/0206
66/193
4,909,244 A * 3/1990 Quarfoot ............... A61F 13/023
428/319.3
(Continued)

FOREIGN PATENT DOCUMENTS

CA 2028529 10/2001
CA 218443 5/2007
(Continued)

OTHER PUBLICATIONS

International Search Report and Written Opinion were mailed on Feb. 28, 2019 by the International Searching Authority for International Application No. PCT/EP2018/084627, filed on Dec. 12, 2018 and published as WO 2019/115645 on Jun. 20, 2019 (Applicant—Mölnlycke Health Care AB) (10 Pages).
(Continued)

*Primary Examiner* — Ophelia A Hawthorne
*Assistant Examiner* — Gina McCarthy
(74) *Attorney, Agent, or Firm* — Ballard Spahr LLP

(57) ABSTRACT

A medical dressing is described for prevention of pressure ulcers. The dressing has a gel pad having a low compressive strength; i.e. from 5 kPa to 60 kPa at a strain of 50%, as measured by the compression test described herein. The dressing reduces the shear and compression forces on the skin and in the underlying the soft tissue layers and prevents or mitigates the onset of pressure ulcers.

21 Claims, 12 Drawing Sheets

(51) Int. Cl.
*A61F 13/00* (2024.01)
*A61F 13/0246* (2024.01)
*A61F 13/05* (2024.01)
*A61L 15/24* (2006.01)
*A61L 15/26* (2006.01)
*A61L 15/42* (2006.01)

(52) U.S. Cl.
CPC .......... *A61F 13/0246* (2013.01); *A61F 13/05* (2024.01); *A61L 15/24* (2013.01); *A61L 15/26* (2013.01); *A61L 15/42* (2013.01); *A61F 2013/00246* (2013.01); *A61F 2013/00404* (2013.01)

(58) Field of Classification Search
CPC .. A61F 13/0226; A61F 13/0246; A61F 13/06; A61F 5/01; A61F 5/30; A61F 5/34; A61F 2013/00748; A61F 2013/00089; A61F 2013/00246; A61F 2013/00361; A61F 2013/00365; A61F 2013/00387; A61F 2013/00404; A61F 13/069; A61F 13/0233; A61F 13/0259; A61F 13/53713; A61F 13/476; A61F 13/15; A61L 15/07; A61L 15/60; A61L 15/20; A61L 15/26; A61L 15/46; A61M 1/87; C08G 18/14; C08L 33/24; D04H 1/4291
See application file for complete search history.

(56) References Cited

U.S. PATENT DOCUMENTS

| | | | | |
|---|---|---|---|---|
| 5,056,510 A * | 10/1991 | Gilman | ............... | A61F 13/0246 D24/189 |
| 5,056,511 A | 10/1991 | Ronge et al. | | |
| 5,056,512 A | 10/1991 | Bower et al. | | |
| 5,700,254 A * | 12/1997 | McDowall | ........ | A61F 13/15699 604/378 |
| 5,704,905 A * | 1/1998 | Jensen | ................ | A61F 13/0213 602/42 |
| 5,788,684 A * | 8/1998 | Abuto | ............... | A61F 13/53713 604/378 |
| 5,973,221 A * | 10/1999 | Collyer | ................... | A61L 15/26 602/56 |
| 6,040,493 A * | 3/2000 | Cooke | ..................... | A61L 15/20 602/41 |
| 8,759,454 B2 * | 6/2014 | Kwon | ..................... | C08G 18/44 427/353 |
| 10,080,555 B2 * | 9/2018 | Llinas | ................. | A61F 13/0213 |
| 10,973,692 B2 * | 4/2021 | Rule | ..................... | A61F 13/0233 |
| 11,890,170 B2 | 2/2024 | Rodzewicz | | |
| 2001/0041933 A1 * | 11/2001 | Thoma | ..................... | A61L 27/18 623/2.36 |
| 2002/0193767 A1 * | 12/2002 | Mavinkurve | ........ | A61F 13/476 604/385.04 |
| 2003/0082966 A1 * | 5/2003 | Menday | ................... | A61F 13/15 428/36.1 |
| 2003/0225356 A1 | 12/2003 | Kulichikhin et al. | | |
| 2004/0049146 A1 * | 3/2004 | Kolte | ................. | A61F 13/0203 602/61 |
| 2004/0138604 A1 | 7/2004 | Sigurjonsson et al. | | |
| 2004/0162512 A1 * | 8/2004 | Liedtke | ............... | A61F 13/0259 602/42 |
| 2005/0059918 A1 | 3/2005 | Sigurjonsson et al. | | |
| 2007/0083141 A1 * | 4/2007 | Flam | ..................... | A61F 13/069 602/61 |
| 2008/0039759 A1 * | 2/2008 | Holm | ................... | A61F 13/0226 602/41 |
| 2009/0148394 A1 * | 6/2009 | Munro | ..................... | A61P 17/02 424/78.05 |
| 2009/0177135 A1 | 7/2009 | Rogers et al. | | |
| 2009/0187130 A1 * | 7/2009 | Asmus | ..................... | A61L 15/46 602/42 |
| 2010/0211029 A1 * | 8/2010 | Tsai | ......................... | A61M 1/87 604/319 |
| 2012/0029455 A1 * | 2/2012 | Perez-Foullerat | ........................... | A61F 13/0203 156/60 |
| 2013/0053747 A1 | 2/2013 | Lin | | |
| 2013/0096478 A1 * | 4/2013 | Cureton | .............. | A61F 13/0213 602/43 |
| 2013/0138068 A1 | 5/2013 | Hu et al. | | |
| 2014/0107561 A1 | 4/2014 | Dorian et al. | | |
| 2017/0135862 A1 | 5/2017 | Tuck | | |
| 2020/0115539 A1 * | 4/2020 | Kudo | ....................... | C08L 33/24 |
| 2020/0255992 A1 * | 8/2020 | Parsons | ................. | D04H 1/4291 |

FOREIGN PATENT DOCUMENTS

| | | |
|---|---|---|
| CN | 102209508 | 10/2011 |
| EP | 2001424 | 12/2008 |
| EP | 3085344 | 10/2016 |
| EP | 3260098 | 12/2017 |
| EP | 2829287 | 7/2019 |
| GB | 1049196 | 11/1966 |
| JP | 2014/168573 | 9/2014 |
| WO | WO 1996/10972 | 4/1994 |
| WO | WO 0132121 | 5/2001 |
| WO | WO 2001/96422 A1 | 12/2001 |
| WO | WO 2007/113597 | 10/2007 |
| WO | WO 2008/149107 A1 | 6/2008 |
| WO | WO 2010/048078 | 4/2010 |
| WO | WO 2012/048128 A2 | 4/2012 |
| WO | WO 2014/058532 | 4/2014 |
| WO | WO 2016/030047 | 3/2016 |

OTHER PUBLICATIONS

European Search Report and Written Opinion were mailed on Feb. 26, 2018 by the European Patent Office for EP Application No. 17207749.7, filed on Dec. 15, 2017 and published as EP 3498241 A1 on Jun. 19, 2019 (Applicant—Mölnlycke Health Care AB) (7 Pages).

European Search Report and Written Opinion were mailed on Apr. 9, 2018 by the European Patent Office for EP Application No. 17207759.6, filed on Dec. 15, 2017 and published as EP 3498244 A1 on Jun. 19, 2019 (Applicant—Mölnlycke Health Care AB) (11 Pages).

International Search Report and Written Opinion were mailed on Mar. 4, 2019 by the International Searching Authority for International Application No. PCT/EP2018/084623, filed on Dec. 12, 2018 and published as WO 2019/115643 on Jun. 20, 2019 (Applicant—Mölnlycke Health Care AB) (14 Pages).

Levy, Ayelet, et al.. The contribution of a directional preference of stiffness to the efficacy of prophylactic sacral dressings in protecting healthy and diabetic tissues from pressure injury: computational modelling studies. Int Wound J., 2017, pp. 1370-1377.

* cited by examiner

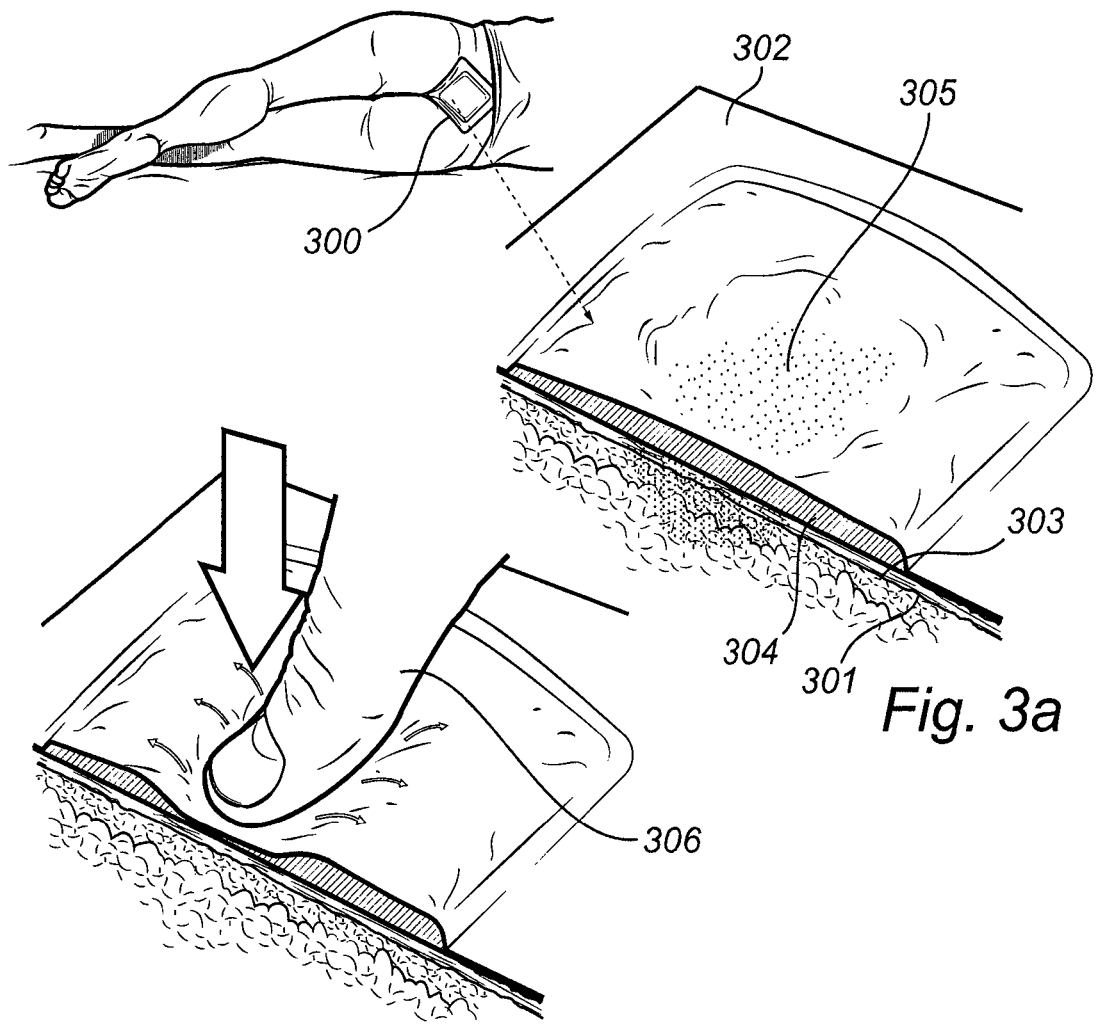
Fig. 3a
Fig. 3b
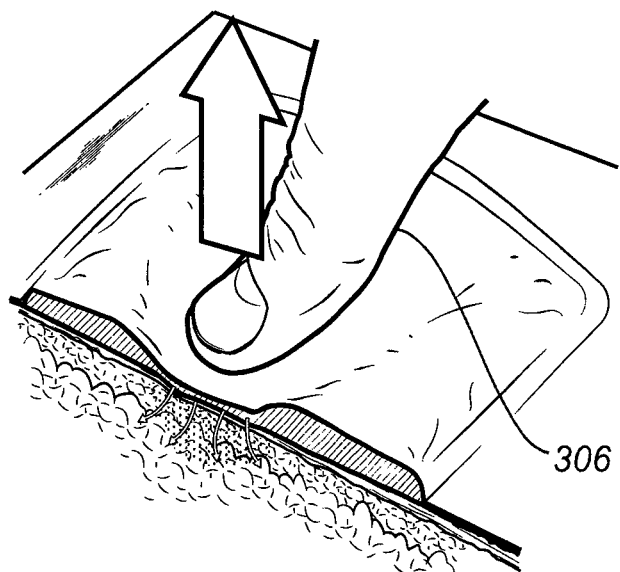
Fig. 3c

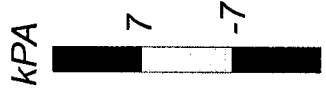
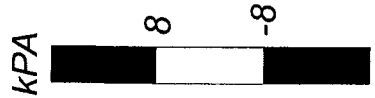

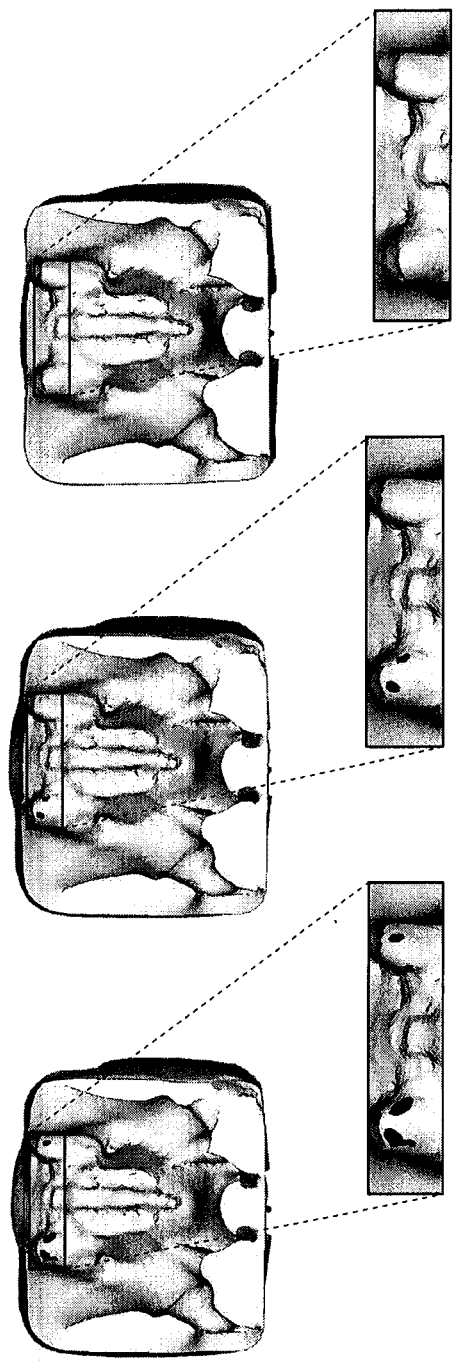
Fig. 12a  Fig. 12b  Fig. 12c

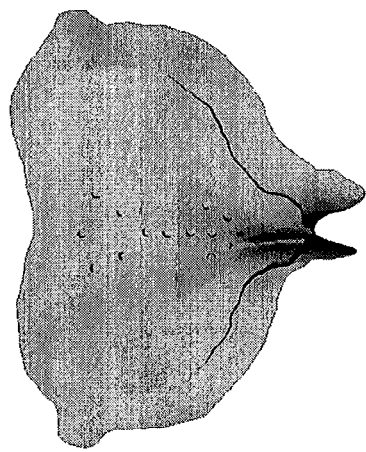
Fig. 13a
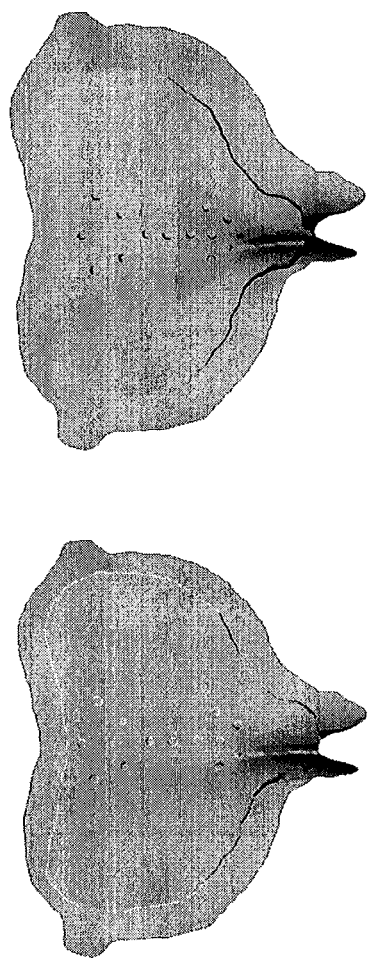
Fig. 13b
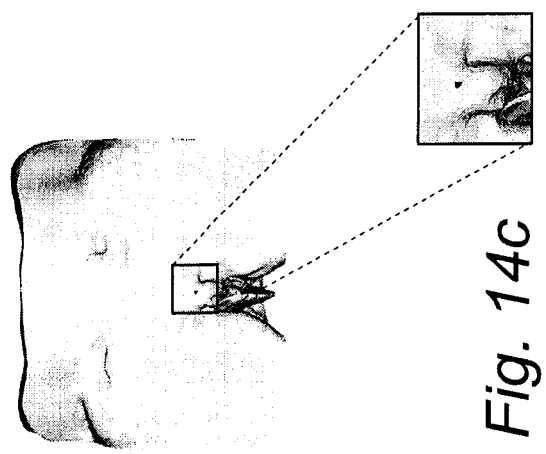
Fig. 14a
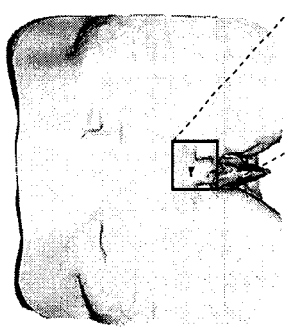
Fig. 14b
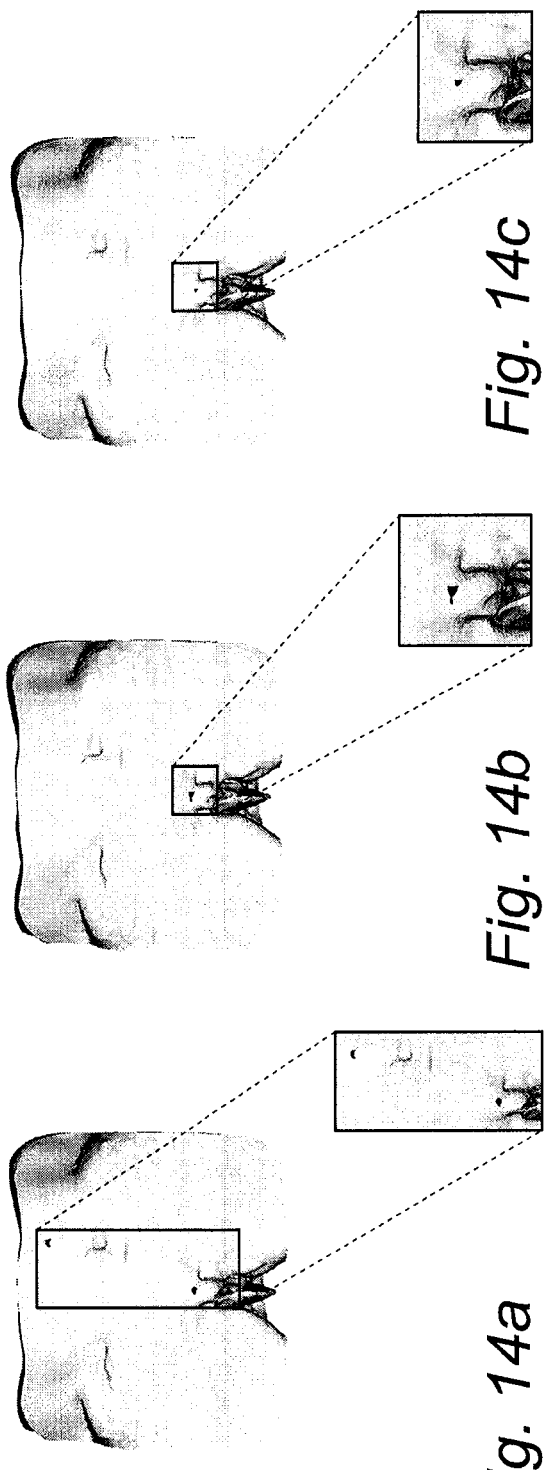
Fig. 14c
kPA 7,5 -7,5

PROPHYLACTIC DRESSING

CROSS-REFERENCE TO RELATED APPLICATIONS

This application is a U.S. National Phase Application of International Application No. PCT/EP2018/084627, filed Dec. 12, 2018, which claims priority to European Application Nos. 17207749.7, filed Dec. 15, 2017, and 17207759.6, filed Dec. 15, 2017, each of which are hereby incorporated by reference in their entirety.

TECHNICAL FIELD

The present invention relates to a medical dressing comprising a gel pad. The dressing is suitable for the prevention of pressure ulcers.

BACKGROUND

A pressure ulcer is a localized injury to the skin and/or underlying tissue over a bony prominence that results from sustained pressure, often in combination with friction and shear. The major factors leading to pressure ulcers or pressure injuries are pressure, shear, friction and unfavorable microclimate. Other factors, intrinsic to patients, may also increase the likelihood of pressure ulcer development, e.g. poor perfusion, reduced sensation and inadequate nutrition. Pressure ulcers often arise among persons being bedridden for various reasons, such as for instance due to long term hospitalization or other causes of immobility. Pressure ulcers also occur beneath medical devices, such as nasogastric tubes, ventilation masks and tracheostomy tubes, which are applied for diagnostic or therapeutic purposes. The rigid materials used in these devices may abrade the skin and create pressure on the soft tissues.

A pressure ulcer does not always start at the skin surface. What is observed at the skin is often only a small part of the sore, and this may mislead the patient or his/her caregiver to believe that there is only a minor problem.

Pressure ulcers often develop in soft tissue under the skin which covers bony areas of the body (so called "bony prominences"), for example the heels, ankles, the hips or the sacrum. Pressure and shear forces cause blood vessels to become squeezed between the skin surface and bone. Hence, muscles and tissue under the skin near the bone surface typically suffer the greatest damage. Accordingly, any pressure ulcer as apparent on the skin, regardless of how small, should be regarded as critical because of the probable damage below the skin surface.

A pressure ulcer can be classified into four categories: in the first category, the skin appears pink, reddened or discoloured, and may feel hard and warm to touch. In the second category, the skin breaks open and an ulcer that may look like a blister is formed. In this stage, the skin may be damaged beyond repair or may die. A category 3 pressure ulcer is an ulcer that extends into the tissue beneath the skin, forming a small crater. In category four, the pressure sore is very deep, reaching into the muscle and bone and causing extensive damage to deeper tissue and tendons. Serious complications, such as infection of the bone or blood can occur if the pressure ulcer progresses.

One of the first signs that a pressure ulcer has developed or is about to develop is a reddened, discolored or darkened skin area. In order to check if a pressure ulcer has developed, caregivers typically use the so called "blanching test", wherein one finger is used to press the darkened or reddened area. The area should go white, and when pressure is removed, the area should return to the red or darkened color within a few seconds, which is an indication of good blood flow. If the area stays white, the blood flow has been impaired and damage has begun.

In a hospital or care facility, caregivers adhere to specific protocols to prevent the occurrence of pressure ulcers. One important part in the prevention regimen is regular inspection of the skin.

In some hospitals, caregivers apply wound dressings to areas at risk of developing pressure ulcers, for example in the sacrum, at the heels or under medical devices such as oxygen masks, and feeding, tracheostomy and nasogastric tubes. The dressings used are not primarily designed for prophylactic purposes.

Furthermore, when a dressing has been applied, the skin underneath the dressing must be regularly inspected, typically at least twice a day, to assess the skin status and ensure that there is no sign of damage. This requires the dressing to be peeled back to allow for assessment of the skin. The dressing may need to be opened up and re-applied several times during the day. The adhesive capacity of dressing is thus impaired.

Pressure ulcers are a global problem and the possibility to prevent these is desirable both to reduce human suffering but also to avoid unnecessary costs. The average cost for a category 3 or 4 pressure ulcer is estimated to be from 75000 to 125000 US dollars per patient.

To summarize, there is a need to provide a dressing having an improved prophylactic effect; i.e. a dressing aimed at preventing a pressure ulcer from occurring in the first place and for preventing the progress of an already existing pressure ulcer. Furthermore, there is a need to provide for a proactive and cost-efficient means to minimize the burden for caregivers and staff dealing with pressure ulcers.

SUMMARY

According to at least one aspect of the invention, there is provided a medical dressing having a first side and a second opposing side, wherein the first side has a skin-facing surface adapted to detachably adhere the medical dressing to a dermal surface; the dressing comprising a gel pad, wherein the gel has a compressive strength of from 5 to 60 kPa at a strain of 50%, as measured according to the compression test described herein.

According to at least one alternative aspect of the invention, there is provided a medical dressing having a first side and a second opposing side, wherein the first side has a skin-facing surface adapted to detachably adhere the medical dressing to a dermal surface; the dressing comprising a gel pad, wherein the gel has a compressive strength of from 1 to 14 kPa at a strain of 25%, as measured according to the compression test described herein.

According to at least one alternative aspect of the invention, which may also be combined with the other two aspects outlined above, there is provided a medical dressing having a first side and a second opposing side, wherein the first side has a skin-facing surface adapted to detachably adhere the medical dressing to a dermal surface; the dressing comprising a gel pad, wherein the gel has a water content of less than 15% by weight.

Any of these (alternative) embodiments may be combined, independently, with any of the subsequent embodiments, including embodiments of the claims.

The medical dressing is particularly useful for pressure ulcer prevention and/or pressure ulcer mitigation. The gel pad of the dressing is soft and pliable and has a consistency that mimics the soft tissue of a human. The inventors have found that by applying a gel dressing having a compressive strength which resembles the compressive strength of human soft tissue to the surface of the skin, critical compression and shear forces on the skin and in the underlying tissue may be reduced. Accordingly, skin cells and soft tissue cells are protected from becoming deformed which may mitigate and/or prevent the onset of pressure ulcers. The gel pad is believed to act as an extra protective soft tissue layer that absorbs pressure, shear and friction forces and distributes these evenly over the gel pad. The dressing of the invention allows for improved protection of the soft tissue under the skin. Furthermore, the pliable and soft gel conforms to the skin and compensates for the asymmetries of the body.

In embodiments, the gel has a compressive strength of from 5 to 40 kPa at a strain of 50%, as measured according to the compression test described herein In embodiments, the gel has a compressive strength of from 2 to 12 kPa, preferably from 2 to 8 kPa at a strain of 25%, as measured according to the compression test described herein.

A pad with a gel having a compressive strength in that range provides improved soft tissue mimicking and prevention of soft tissue damage. If the gel is too soft, the pad may lose efficiency and either break or flatten out in critical areas.

A dressing in use, for example applied to the sacrum region of a patient, is exposed to pressure, shear and compression forces and therefore needs to maintain a low compressive strength at higher strains. It is important that the elastic behavior of the gel does not lead to a dramatic increase of the compressive strength at higher strains. The compressive strength of the gel should increase in a generally smooth manner at strains up to 50%, so that the dressing can still compress at higher loads. It is desired that compression takes place in the dressing and by that reducing the compression and stresses in the tissue. A stiffer dressing does not deform easily and the deformation may therefore be transferred to the tissue, which is undesirable.

In embodiments, the gel has a water content of less than 10% by weight, preferably less than 5%

This enables the dressing to be stored in ambient conditions without requiring special packaging (such as aluminum, hermetically sealed packages etc.), and without compromising the properties of the gel and the dressing. If the water content is too high, the gel may dry out when stored in ambient conditions, which may harden the gel. Instead, standard packaging and ethylene oxide (EtO) sterilization may be used to sterilize the product.

The gel according to the present invention may be manufactured by polymerizing:
15-50% by weight of a hydrophilic acrylic monomer
50-85% by weight of a hydrophilic softening agent
0.001-0.5% by weight of a crosslinker
0.05-0.5% by weight of a polymerization initiator The hydrophilic acrylic monomer(s) is (are) preferably selected from 4-hydroxybutyl acrylate, methoxy polyethylene glycol acrylate, 2-hydroxyethyl acrylate, hydroxypropyl acrylate or combinations thereof.

The monomer(s) is/are chosen so that the co-polymer as formed is hydrophilic, soft, elastic and compatible with the softening agent. The components of the mixture are chosen such that the gel maintains its low compressive strength and softness.

The hydrophilic softening agent is any additive that increases the softness of the gel. In embodiments of the invention, said hydrophilic softening agent is a liquid with low volatility or a solid compound.

In embodiments, the dressing is substantially transparent.

The gel pad, and if present, additional components of the dressing, is/are preferably transparent. This is to enable visual inspection of the skin underneath the dressing. The softness and pliability of the gel, combined with the transparency, allows a caregiver to perform the blanching test on a patient without even having to remove the dressing. One finger can be used to press the skin through the pliable gel pad, and the whiteness and/or redness of the skin can be monitored through the dressing. Although, the dressing still may need to be opened up from time to time, the transparency of the dressing reduces the frequency of detachment and re-application onto the skin of a wearer. Accordingly, the inventive dressing will have a longer wear time, and the patient will be exposed to less invasive examinations. This means time savings and a higher possibility of compliance in a hospital or community care unit. Furthermore, marks can be made on the dressing (or photographs taken) to be able to compare size of redness at the next assessment. The transparency of the dressing allows for the patient and his/her relatives to inspect themselves, and the chances of earlier detection of damage are higher.

In embodiments, the gel pad has an opacity of less than 25%, preferably less than 15%, as measured by the opacity test described herein.

This allows for optimal inspection of the skin beneath the dressing, and any discoloration or reddened part of the skin may be detected.

In embodiments, the dressing comprises a backing layer and an adhesive body contact layer; the gel pad being arranged between the backing layer and the body contact layer.

In embodiments, the dressing adheres to the skin during use, both to increase the stay-on ability of the dressing, but also to prevent undesirable friction between the skin of the patient and the dressing. The skin-facing surface of the gel may be adhesive per se, but the dressing may also comprise an additional adhesive body contact layer. The adhesive body contact layer reduces or eliminates friction on the patient's skin.

In embodiments, the backing layer extends beyond the periphery of the gel pad to define a border portion around the contour of the pad.

The dressing may comprise a border portion to prevent the compliable gel from bulging out in the edges (due to compression or swelling) and to improve the wear and tear of the dressing.

In embodiments, the dressing comprises an anisotropic layer having a first direction (x) and a second direction (y), wherein the anisotropic layer has a higher tensile force at 15% strain in the second direction (y) than in the first direction (x), as measured by the tensile test described herein.

Consequently, the dressing will have a higher tensile force in the second direction (y). In use, the dressing should be applied such that its second direction (y) corresponds to the direction of which the patient is exposed to most shear forces. For example, when the dressing is applied to the sacral region of a bedridden patient, the dressing is stiffer in the direction in which the patient slides in bed. This is normally along the length of the patient. The inventors have found that in order to withstand the pressure and shear forces inflicted on a patient laying on a hospital bed (e.g. a bedridden patient), the dressing should be stiffer, i.e. have a higher tensile force in the direction in which the patient slides. On the other hand, the first direction (x) of the dressing is preferably more pliable and may have a lower tensile force. This is beneficial since the first direction (x) of the dressing corresponds to the direction in which the patient, wearing such dressing, will be turned and re-positioned by nursing personnel. The dressing is advantageously more stretchable in the first direction (x). A bedridden patient at risk of developing pressure ulcers must be turned and repositioned at regular intervals. It is therefore advantageous that the dressing conforms to this lateral movement and stays on the skin.

Furthermore, when the dressing is more stretchable in the first direction (x), it prevents the skin and underlying tissues from becoming "over constrained" which could otherwise be the case when the dressing is stiff in both the first (x) and the second (y) directions.

In embodiments, the anisotropic layer has a tensile force at 15% strain that is at least 6 times higher, preferably at least 10 times higher in the second direction (y) than in the first direction (x), when measured according to the tensile test described herein.

The prophylactic effect of the dressing is thereby improved, and the skin cells and underlying soft tissue cells are protected from becoming extensively damaged. The structural integrity of the dressing is improved, and the pressure and shear forces inflicted on a patient are reduced. Stiffness in the direction of critical shear exposure protects the skin cells and deeper tissue layer cells from stretching, and thereby deforming. Sustained deformation of skin and tissue cells may affect the tissue in various ways; i.e. impaired cell metabolism resulting from vascular occlusion leading to ischemia, impaired membrane transport of the individual deformed cells, tears in-between cells, all of which may result in tissue and cell damage resulting in the formation of pressure ulcers.

The sacral region is an area at particular risk for pressure ulcers. Therefore, in embodiments, the dressing has a shape that conforms to the anatomy of the sacrum.

Hence, the dressing has a lateral (x) extension and a longitudinal (y) extension; the pad being symmetric about a longitudinal center line and the dressing comprising a first lobed portion on one side of the longitudinal center line and a second lobed portion on the other side of the longitudinal center line.

In embodiments, the anisotropic layer is arranged such that the first direction (x) of the anisotropic layer corresponds to the lateral (x) extension of the dressing, and the second direction (y) of the anisotropic layer corresponds to the longitudinal (y) extension of the dressing.

As explained hereinbefore, the dressing protects the skin cells and deeper tissue layer cells from stretching and becoming deformed. It also improves the stay-on ability of the dressing if the dressing is more stretchable in the lateral (x) direction enabling patient turning and re-positioning without the dressing falling off.

In embodiments, the medical dressing is divided into three separate zones along the longitudinal (y) extension of the dressing: one central zone and two lateral zones, wherein the gel pad comprises a plurality of indentations, at least in the central zone of the dressing.

The central zone of the dressing is the area exposed to most stresses, especially in the lower part of the central zone which is arranged to cover the coccyx region of a patient. The indentations allow for a localized softening of the gel pad while preserving the overall properties of the gel dressing. The inventors have found that the skin and the soft tissue underneath is better protected by the provision of indentations in the central zone.

In embodiments, the medical dressing is divided into three separate zones along the longitudinal (y) extension of the dressing: one central zone and two lateral zones, wherein the compressive strength of the gel in the central zone is lower than in the lateral zones.

Accordingly, the dressing may be formed of different regions having different properties; i.e. compressive strengths. As mentioned, the central zone is exposed to the most stresses when the dressing is in use. The inventors have found that this region may be softer, i.e. have a lower compressive strength to prevent the soft tissue cells from becoming deformed and damaged. Accordingly, the central dressing zone may have a compressive strength in the range specified above, and the lateral zones of the dressing may have a higher compressive strength. This may be beneficial to avoid flattening of the gel pad in the edges.

The medical dressing may still need to be opened up from time to time. Therefore, to facilitate inspection of the skin, the dressing may comprise at least one gripping tab, wherein the tab is coplanar with and projects outwardly from the periphery of the dressing.

The gripping tab guides the caregiver to lift the dressing, inspect the skin underneath the dressing, and to thereafter re-apply the dressing onto the skin.

In another aspect, the present invention relates to a dressing as described hereinbefore for use in the prevention or mitigation of pressure ulcers.

Further features of, and advantages with, the present invention will become apparent when studying the appended claims and the following description. The skilled addressee realizes that different features of the present invention may be combined to create embodiments other than those described in the following, without departing from the scope of the present invention.

BRIEF DESCRIPTION OF THE DRAWINGS

FIG. 3a illustrates a zoomed in view of a medical dressing according to at least one exemplary embodiment of the invention, applied to the sacrum region of a human body and illustrates an area where the blanching test is to be performed.

FIG. 3b illustrates a zoomed in view of a medical dressing according to at least one exemplary embodiment of the invention, applied to the sacrum region of a human body and illustrates a caregiver performing the blanching test on the patient's skin.

FIG. 3c illustrates a zoomed in view of a medical dressing according to at least one exemplary embodiment of the invention, applied to the sacrum region of a human body and illustrates a caregiver performing the blanching test on the patient's skin.

FIG. 12a illustrates the shear stress distribution at the muscle next to the bones arising from compression and shear in a Finite element (FE) model simulation, when no dressing is used.

FIG. 12b illustrates the shear stress distribution at the muscle next to the bones arising from compression and shear in a Finite element (FE) model simulation, when two dressings according to exemplary embodiments of the present invention are used.

FIG. 12c illustrates the shear stress distribution at the muscle next to the bones arising from compression and shear in a Finite element (FE) model simulation, when two dressings according to exemplary embodiments of the present invention are used.

FIG. 13a illustrates a simulated dressing with a central pad zone comprising apertures.

FIG. 13b illustrates a simulated dressing with a central pad zone comprising apertures and a lower compressive strength region.

FIG. 14a illustrates the Von Mises stress distribution at the muscle arising from compression in a Finite element (FE) model simulation, when no dressing is used.

FIG. 14b illustrates the Von Mises stress distribution at the muscle arising from compression in a Finite element (FE) model simulation, when the dressings illustrated in FIG. 13a and FIG. 13b are used.

FIG. 14c illustrates the Von Mises stress distribution at the muscle arising from compression in a Finite element (FE) model simulation, when the dressings illustrated in FIG. 13a and FIG. 13b are used.

DETAILED DESCRIPTION

The present invention will now be described more fully hereinafter with reference to the accompanying drawings, in which currently preferred embodiments of the present invention are shown. The present invention may, however, be embodied in many different forms and should not be construed as limited to the embodiments set forth herein; rather, these embodiments are provided for thoroughness and completeness, and to more fully convey the scope of the present invention to the skilled person.

Figure 1A:
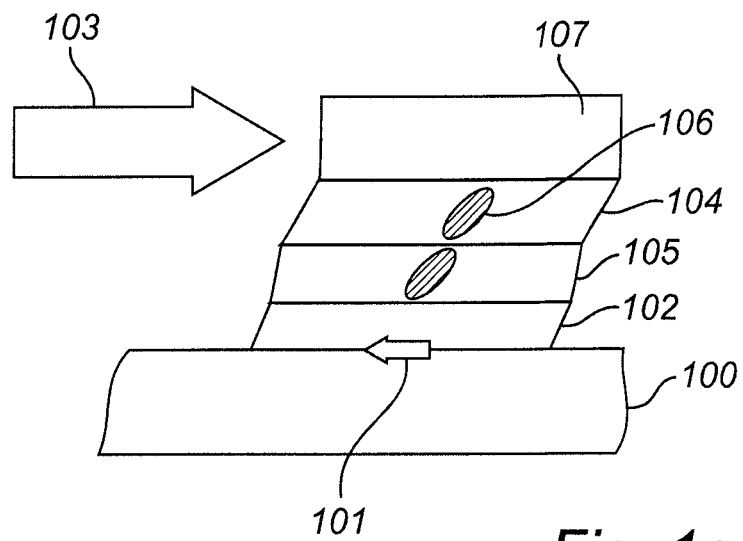
FIGS. 1a and 1b schematically illustrate how pressure, shear and friction contribute to the development of pressure ulcers.
Figure 1B:
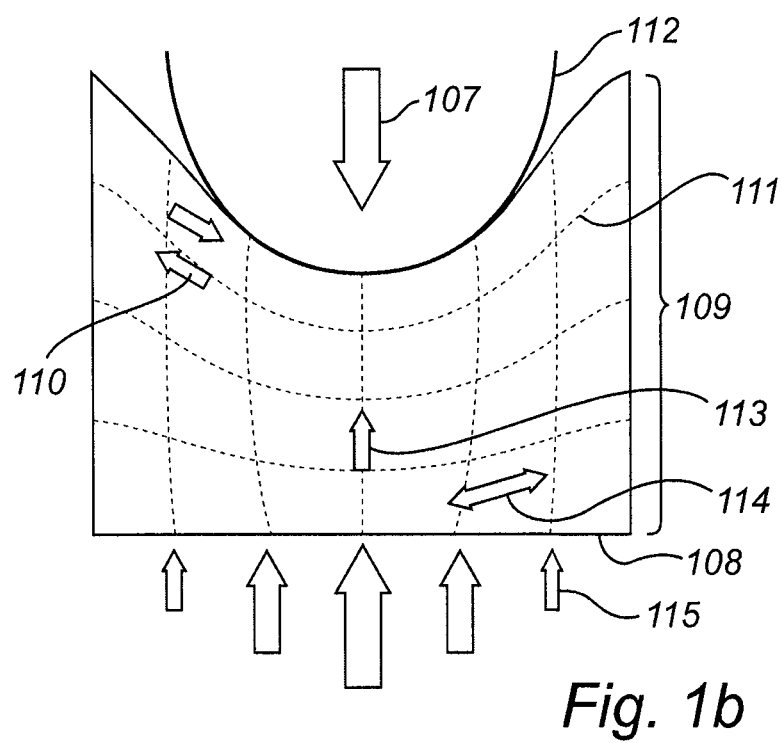

FIGS. 1a and 1b conceptually illustrate how pressure, shear and friction contribute to pressure ulcer development.

When a patient in contact with a support surface 100 moves, friction 101 between the skin 102 and the support surface 100 tends to hold the skin 102 in place and a shear force 103 occurs that displaces and deforms the deeper tissues (muscle 104 and adipose tissue 105). The deeper tissue layers 104 and 105 are subject to the worst effect of shear since these layers, in closer proximity to the bone 107, cannot move in a manner like the skin layer 102 does. Instead these layer are stretched but still "stuck". Furthermore, blood vessels 106 are distorted and compressed (FIG. 1a). Compression of blood vessels 106 by pressure and/or shear may reduce the blood flow to tissues. This may result in tissue hypoxia, build-up of metabolic waste products and, eventually, tissue damage.

Referring to FIG. 1b, when a force 107 is applied perpendicular to the surface of the skin, pressure is exerted onto the skin 108 and subcutaneous tissues 109. Pressure 107 compresses the tissues 109 and may distort or deform the skin and the soft tissues (e.g. subcutaneous fat and muscle). Shear 110 may also occur in and between layers 111 of deeper tissues as a result of tissue deformation caused by pressure over a bony prominence 112. Muscle is particularly prone to damage by shear. Compression stresses 113 occur in the axis perpendicular to the direction of the muscle fibers, and tensile stresses 114 occur when the tissue is stretched and deformed along the fiber direction. The arrows 115 represent surface pressure. Deformation of soft tissues is greater when pressure is applied over a bony prominence 112. Damage thus often occurs initially in the soft tissue, i.e. at the muscle/bone interface, and skin breakdown and pressure sore formation occurs later in the process. Hence, when assessing a pressure sore, the full extent of the damage may not be clear or visible.

Figure 2:
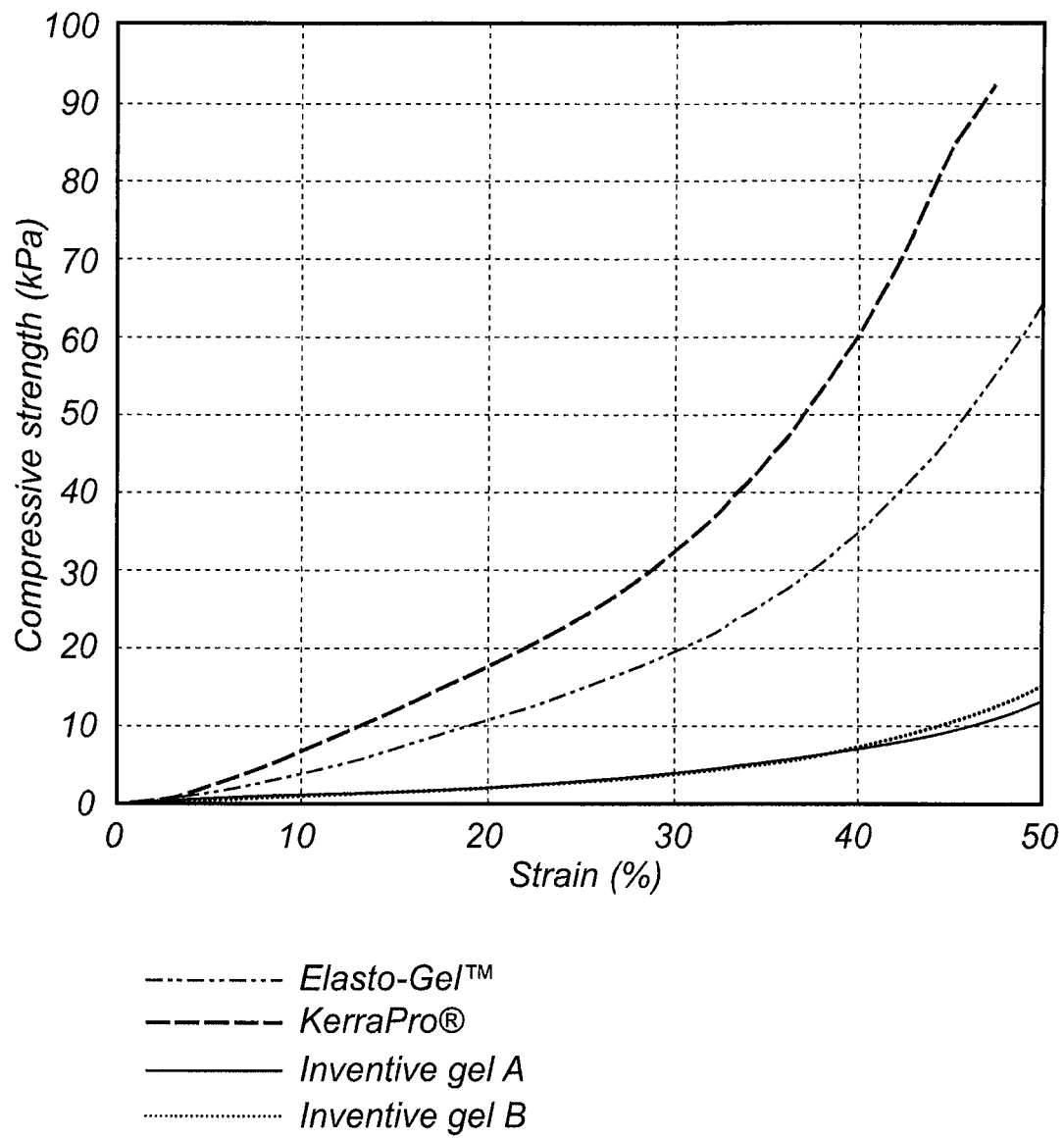
FIG. 2 illustrates the compressive behaviour of two dressings according to the invention compared with two more rigid dressings according to prior art.

FIG. 2 illustrates the compressive behavior of two gel dressings according to the present invention and two prior art dressing comprising more rigid gel pads, at different strains. The compressive strength (y axis) refers to the amount of stress required to deform a material at a certain strain (x axis).

The inventive gels A and B follow a compressive strength curve that closely resembles, respectively, the behavior of soft tissue. At low strains, the soft tissue has a linear compressive behavior with a compressive strength close to 2 kPa at 20% strain, but its compressive strength increases dramatically at higher strains (above 40%) due to the hyperelastic properties of the soft tissue. The inventive gels A and B in FIG. 2 show a similar linear behavior at lower strains, and the compressive strength curves remain substantially linear even at strains up to 50%.

This behavior is advantageous for the purpose of preventing and/or mitigating pressure ulcers. The soft tissue underneath the dressing is protected from becoming damaged and deformed, and the gel pad may reduce pressure, shear and friction forces occurring at the skin and in the soft tissue layers. The gel dressings of the present invention allow for compression at high loads. The low compressive strength of the gel at higher strains (50%) prevents deformation (resulting from compression) to be transferred to the underlying skin and soft tissue. Instead deformation due to high load is taking place within the dressing.

Measuring the compressive strength at a strain of 50% is a particularly useful point in the compressive strength (strain)-curve (see FIG. 2) as the compression at this strain represents the compression that a bed-ridden patient is typically exposed to in a clinical setting.

FIGS. 3a-3c illustrate a dressing 300 according to an exemplary embodiment of the present invention, applied to the skin in the sacrum region of a patient. The medical dressing 300 has a first side 301 and a second opposing side 302, wherein the first side 301 has a skin-facing surface 303 adapted to detachably adhere the medical dressing 300 to a dermal surface; the dressing comprising a gel pad 304, wherein the gel has a compressive strength of from 1 to 14 kPa at a strain of 25%, as measured according to the compression test described herein.

In embodiments, the gel has a compressive strength of from 5 to 60 kPa, preferably from 5 to 40 kPa at a strain of 50%, as measured according to the compression test described herein.

Most preferably, the compressive strength of the gel is less than 25 kPa at a strain of 50%, as measured according to the compression test described in the specification.

Suitably, the compressive strength is from 2 to 12 kPa, or from 2 to 8 kPa at a strain of 25%, as measured according to the compression test described herein.

As used herein, the term "compressive strength" refers to the amount of stress required to deform the material at a certain strain. Compressive strength is calculated by dividing the load by the original cross-sectional area of a specimen. The compressive strength as defined here is independent of the maximum compressive strength before fracture (i.e. the maximal stress that a material can take in before it breaks). The compressive strength is measured as described in the Example section.

In embodiments of the present invention, the gel as described herein has a water content of less than 15% by weight, preferably less than 10% by weight, further preferably less than 5% by weight. In embodiments, the gel has a water content of from 0.5% by weight to 15% by weight, preferably from 1% by weight to 13% by weight, further preferably from 3% by weight to 12% by weight.

It is believed that conventional hydrogels; i.e. gels containing a significant amount of water as described in the art generally are not suitable to be used as gels in accordance with the present invention.

The composition of the gel as described above enables the dressing to be stored in ambient conditions without requiring special packaging (such as aluminum, hermetically sealed packages etc.), and without compromising the properties of the gel and the dressing. If the water content of the gel is too high, the gel may dry out when stored in ambient conditions. As a result, the gel may become stiffer and harder. Instead, standard packaging may be used and ethylene oxide (EtO) sterilization can be used to sterilize the product.

The gel according to the present invention may be manufactured by polymerizing:
  15-50% by weight of a hydrophilic acrylic monomer,
  50-85% by weight of a hydrophilic softening agent,
  0.001-0.5% by weight of a crosslinker,
  0.05-0.5% by weight of a polymerization initiator.

The hydrophilic acrylic monomer(s) is (are) preferably selected from monomers yielding a homopolymer with a low glass transition temperature, Tg, such as less than −10° Celsius, preferably less than −20° Celsius.

In embodiments, the hydrophilic acrylic monomer is selected from 4-hydroxybutyl acrylate, methoxy polyethylene glycol acrylate, 2-hydroxyethyl acrylate, hydroxypropyl acrylate or combinations thereof.

The monomer(s) is/are chosen so that the co-polymer as formed is hydrophilic, soft, elastic and compatible with the softening agent. The monomers are typically present in an amount of 15-50% by weight, suitably of 20-35% by weight of the total mixture.

In embodiments, the polymerization mixture further comprises 0.1 to 5% of a monomer containing acidic groups or salts thereof. In embodiments, said monomer is, acrylic acid or, more preferably, 2-acrylamido-2-methylpropane sulfonic acid (AMPS) or salts thereof are used. The monomers containing acidic groups or its salts may enhance the absorption capacity of the gel.

In embodiments, a comparatively low amount of monomers containing acidic groups or its salts, e.g. 2-acrylamido-2-methylpropane sulfonic acid sodium salt (Na-AMPS) is used, such as from 0.1 to 5% by weight, e.g. from 0.1 to 3% by weight, e.g. from 0.1 to 2% by weight. Acrylic acid and AMPS typically yield homopolymers having a higher glass transition temperature, Tg. Hence, if present in too high amounts, the resulting gel may be too hard.

The hydrophilic softening agent may be selected from polyethylene glycol, glycerol and/or urea or combinations thereof. The total amount of softening agent is 50-85% by weight, suitably 65-80% by weight.

The crosslinker is preferably selected from difunctional acrylates, such as polyethylene glycol diacrylate. A small amount, such as from 0.001 to 0.5% by weight is typically used, preferably from 0.001 to 0.2% by weight. A low cross-linking degree is desirable to maintain the softness of the gel.

A polymerization initiator may be an UV initiator selected from 1-hydroxycyclohexyl-phenyl ketone, 2-Hydroxy-2-methylpropiophenone and combinations thereof. The UV initiator allows the gel to be curable in an UV curing process.

In the embodiment illustrated in FIGS. 3a-3c, the gel pad 304 and the dressing 300 are substantially transparent.

As used herein, the term "substantially transparent" means that the dressing is sufficiently transparent to allow visual inspection of the skin; i.e. to monitor potential skin colour changes or ulcer formation without having to remove the dressing from the skin.

Suitably, the gel pad 304 has an opacity of less than 25%, preferably less than 15% as measured by the opacity test described herein.

The opacity of the gel pad reflects the degree of "untransparency" of the gel. When the gel pad has an opacity of 0%, the gel is completely transparent. If the gel pad has an opacity of 100%, the gel pad has no transparency; i.e. no light can be transmitted through the material. The opacity of the gel pad shows the degree on how clearly the skin can be seen through the gel pad. When the opacity is less than 25%, any shift in color or skin appearance can be observed through the dressing. The opacity is measured in according to the standard method ASTM D2244-11 as described in the Example section.

The assessment for potential tissue damage includes an observation of the skin for changes in color compared with the surrounding skin. FIGS. 3a-3c illustrate skin palpation or the so called "blanching test" on a patient. Blanchable redness of the skin (erythema) may signal imminent tissue damage. In FIG. 3a, a reddened area 305 can be observed under the dressing. In a patient with a pressure ulcer, the redness may result from the release of ischemia-causing pressure.

An erythematous lesion that loses all redness when pressed is termed "blanchable". Blanchable erythema is initially red, but turns white when pressed with a fingertip (FIG. 3b), and then turns red again when pressure is removed (FIG. 3c). Skin palpation may be performed through the gel pad 304 without having to remove the dressing 300 from the skin. The caregiver may press his/her finger 306 through the soft and compliable gel 304 and note the color of the skin when the pressure of the finger is removed (FIG. 3c). The gel 304 is so soft and compliable that, when a finger 306 is pressed on the pad portion, it "sinks" into the gel 304, as can be observed in FIG. 3b. Tissue exhibiting blanchable erythema usually resumes its normal color within 24 hours and suffers no long-term damage. The longer it takes for tissue to recover from finger pressure, the higher the patient's risk for developing pressure ulcers.

On the other hand, non-blanchable erythema may be a first sign of tissue destruction. The redness associated with non-blanchable erythema is more intense and does not change when compressed with a finger. If recognized and treated early, non-blanchable erythema is reversible. The medical dressing of the present invention enables such early recognition.

The thickness of the gel pad may vary depending on where the dressing is to be applied. Dressings are available in a variety of sizes and shapes suitable for different anatomical locations. Different anatomical sites vary in skin properties, shape of underlying bony prominence, and thickness and types of subcutaneous tissue present. For example, a heel dressing may be thicker than a dressing applied to the sacrum or the face or head of a patient.

In embodiments, the thickness of the gel pad is in the range of from 2 to 10, e.g. from 2 to 6 mm, suitably from 2 to 4 mm. A gel pad that is too thick may cause increased stresses in the soft tissue.

Figure 4A:
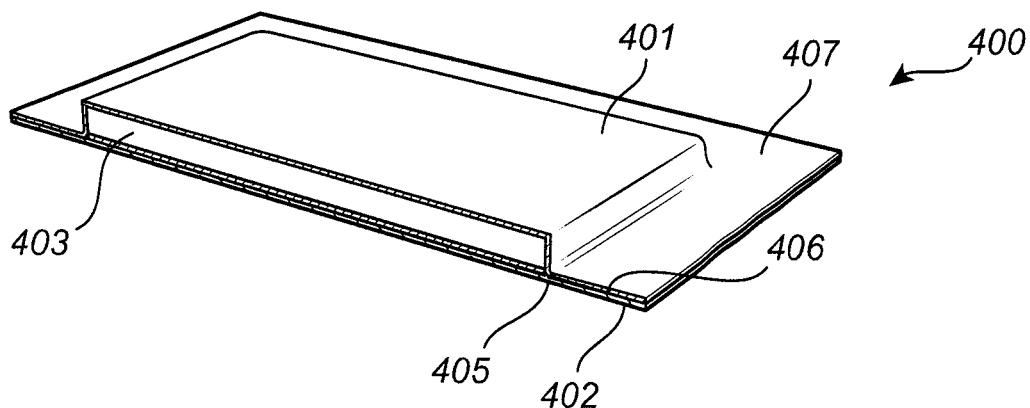
FIG. 4a is a cross-sectional view of a dressing according to one exemplary embodiment of the present invention.

FIG. 4a illustrates a cross-sectional view of an exemplary embodiment of the present invention. The dressing comprises a backing layer 401 and an adhesive body contact layer 402; the gel pad 403 being arranged between the backing layer 401 and the body contact layer 402.

As used herein, the term "body contact layer" means the layer that is in contact with the skin of a wearer. The body-facing surface of the gel can be adhesive per se, but it may also comprise an additional adhesive layer. In the field of medical dressings, in particular, wound dressings, an adhesive film or layer for adhering to the patient is often referred to as a wound contact layer. The present invention is primarily intended for pressure ulcer prevention, i.e. for use on a human body area which is not necessarily in need of wound treatment. Therefore, in this application the adhesive film or layer will be referred to as a body contact layer. However, it should be understood that although the primary use of the invention is pressure ulcer prevention, if nursing personnel decides to use it as a wound dressing, the body contact layer could be applied onto a wound or a scar.

In embodiments, the adhesive body contact layer 402 of the dressing covers at least 60% of the surface of the pad 403. Suitably, the adhesive body contact layer 402 covers at least 75% of the surface of the pad.

It is beneficial to have an even distribution of adhesive over the surface of the pad in order to keep the dressing in place during use. Also, a greater coverage of adhesive on the surface of the pad aids in preventing undesirable friction forces which could form between the skin and the dressing as a patient slides in bed.

The adhesive body contact layer 402 has a body facing surface 405; i.e. a surface oriented towards the skin of the wearer, and a non-body facing surface 406, i.e. a surface oriented opposite to the adhesive surface when fitted to a wearer.

The adhesive body contact layer 402 may comprise a film covered by an adhesive layer (not shown). The film onto which the adhesive layer is applied may be comprised of a thin plastic film, or a laminate comprising a thin plastic film, e.g. a thin polyurethane film having a thickness from 15 and 100 µm, e.g. from 20 to 80 µm, preferably from 45 to 60 µm.

The adhesive is preferably be skin-friendly, and sufficiently adherent to skin such that the dressing stays in place, and maintains its adherence with repeated removal and re-application. The adhesive should be easy to remove without causing trauma and is suitably silicone based. In embodiments of the invention the adhesive may comprise a soft silicone gel.

Examples of suitable silicone gels include the two component RTV systems, such as Q72218 (Dow Corning), and SilGel 612 (Wacker Chemie AG) mentioned herein, as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No 14194054.4. The thickness of the adhesive layer is preferably at least 20 µm.

The adhesive body contact layer may be perforated or non-perforated. The adhesive body contact layer is preferably substantially transparent.

Figure 4B:
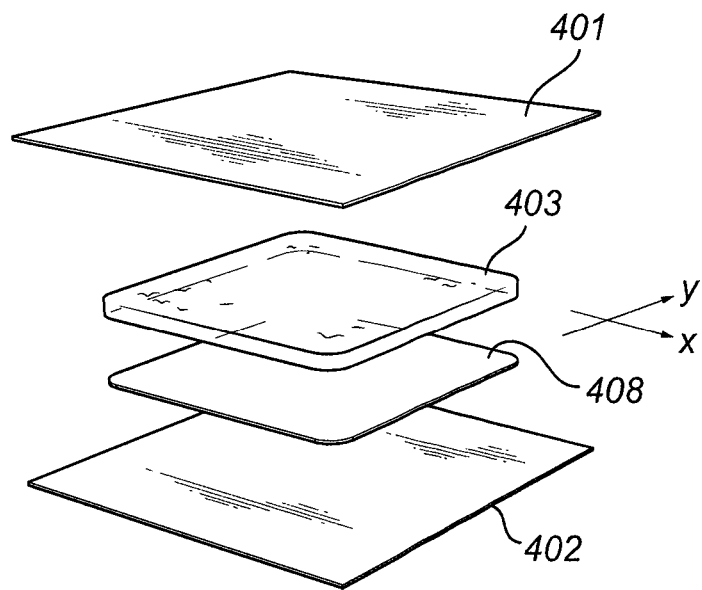
FIG. 4b is a split view of a dressing according to one exemplary embodiment of the present invention.
Figure 4C:
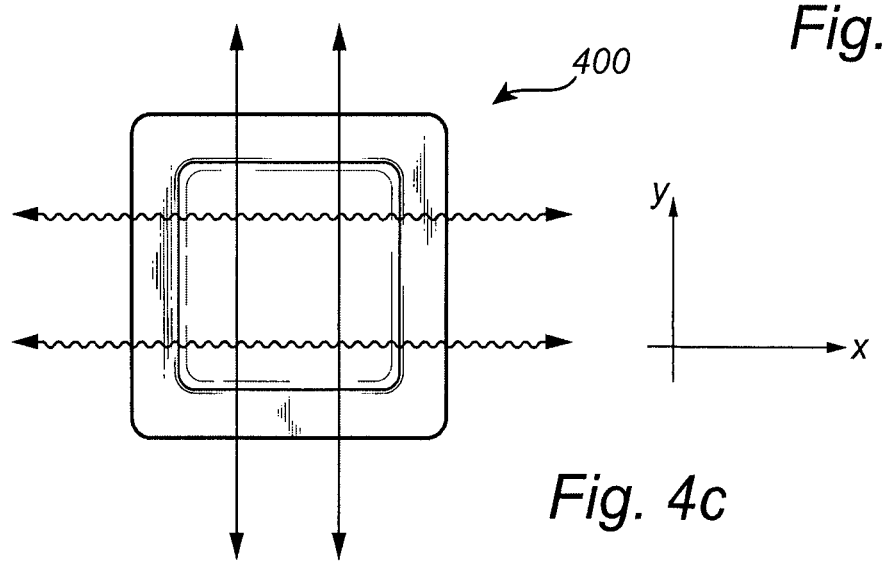
FIG. 4c illustrates the anisotropic properties of a dressing according to one exemplary embodiment of the present invention.

The medical dressing may comprise a border portion 407. In embodiments, at least the backing layer 401 extends beyond the periphery of the gel pad 403 to define a border portion 407 around the contour of the pad 403. In FIGS. 4a-4c, the backing layer 401 and the adhesive body contact layer 402 extend beyond the periphery of the gel pad 403 to define a border portion 407 around the contour of the pad 403. The body contact layer 402 is typically co-extensive with the backing layer 401, and has the same outer dimensions. The border portion 407 forms a closed path around the contour of the pad 403 and the backing layer 401 and body contact layer 402 are bonded to each other in those areas of both layers that extend beyond the periphery of the pad. The adhesive may be a thin acrylic adhesive.

In order to achieve sufficient adhesion properties, the border portion 407 has a width of 5 to 50 mm and extends along the contour of the pad 403. A smaller sized dressing may have a smaller border portion than a larger sized dressing. Preferably the border portion has a width of 10 to 25 mm and extends along the contour of the pad. This allows for easy handling and application of the product while still maintaining sufficient adhesion upon application.

The backing layer 401 may be a thin film, sheet or membrane that is vapour permeable and waterproof. Examples of suitable materials for the backing layer include, but are not limited to polyurethane, polyethylene or polyamide films, silicone films, polyester based nonwoven materials, and laminates of polyester-based nonwoven materials and polyurethane films. Suitably, the backing layer is a polyurethane film having a thickness of from 5 to 40 μm, e.g. from 15 to 25 μm. The backing layer 401 may be partly or fully bonded to the pad 403, for example, via an adhesive such as a pressure sensitive adhesive (e.g. an acrylic adhesive).

Preferably, the backing layer 401 is substantially transparent.

In exemplary embodiments, the dressing 400 comprises an anisotropic layer 408.

As used herein, the term "anisotropic layer" means a layer that has anisotropic stiffness properties; i.e. the stiffness (or stretchability) of the layer is different in the first (x) and the second (y) directions. In the present disclosure, the "anisotropic layer" is stiffer in the second direction (y) and more stretchable in the first direction (x).

The anisotropic layer 408 has a first direction (x) and a second direction (y), wherein the anisotropic layer has a higher tensile force at 15% strain in the second direction (y) than in first direction (x), as measured by the tensile test described herein.

The tensile force at 15% strain in the second direction (y) may be at least 6 times higher, preferably at least 10 times higher than in the first direction (x), as measured by the tensile test described herein.

The anisotropic layer 408 may be a film or a layer having a tensile force at 15% strain of at least 4 N, preferably at least 10 N, and most preferably at least 15 N in the second direction (y), when measured by the tensile test described herein.

The anisotropic layer 408 may be selected from a variety of materials such as nonwovens, films, textile materials, polymeric net materials as long as they exhibit the desired anisotropic stiffness properties. The anisotropic layer 408 may comprise a plurality of reinforcement fibres or filaments extending in the longitudinal direction. The reinforcement fibres or filaments provide the layer with high tensile force in the longitudinal (y) direction. Films or nets made of e.g. polyethylene, polypropylene, polyester, polyurethane or silicone can be used as long as these materials have sufficient strength in the longitudinal direction (y) and sufficient anisotropic properties.

In embodiments, the anisotropic layer 408 comprises a nonwoven. Suitable nonwovens for use as the first anisotropic layer are meltblown, spunbond, spunlaced or carded nonwoven webs.

In exemplary embodiments, the anisotropic layer is an oriented fibrous nonwoven layer having more than 50% of the fibres oriented in the longitudinal (y) direction. In this manner, the fibres oriented in the longitudinal (y) direction will provide reinforcement in this direction.

Examples of suitable polymers for use in the nonwoven are polyethylene, polyesters, polypropylene and other polyolefin homopolymers and copolymers.

For example, nonwoven webs comprising thermoplastic fibres of polypropylene and polyethylene fibres or mixtures thereof may be used. The webs may have a high content of thermoplastic fibres and contain at least 50%, e.g. at least 70% thermoplastic fibres. The nonwoven may be a mixture of polyethylene and viscose, e.g. in a 70:30 ratio. Natural fibres, for example cotton may also be used as long as they provide the desired properties. The basis weight of the nonwoven may be in the range of from 10 to 80 g/m$^2$, e.g. of from 13 to 50 g/m$^2$. The first anisotropic layer may also be a spunbond-meltblown or spunbond-meltblown-spunbond (SMS) web.

Preferably, the anisotropic layer 408 is substantially transparent such that it does not obstruct the transparency of the gel dressing 400. The anisotropic layer may comprise additives to achieve the desired transparency/opacity. For example, organic or inorganic dyes, coloring agents or whitening agents may be used.

The anisotropic layer 408, when present, affects the anisotropic stretching properties of the entire dressing. As illustrated by the arrows in FIG. 4c, the dressing 400 is stiffer in the second direction (y) and more stretchable in the first direction (x).

The effect of this feature may be explained with reference to FIGS. 5a-5b.

Figure 5A:
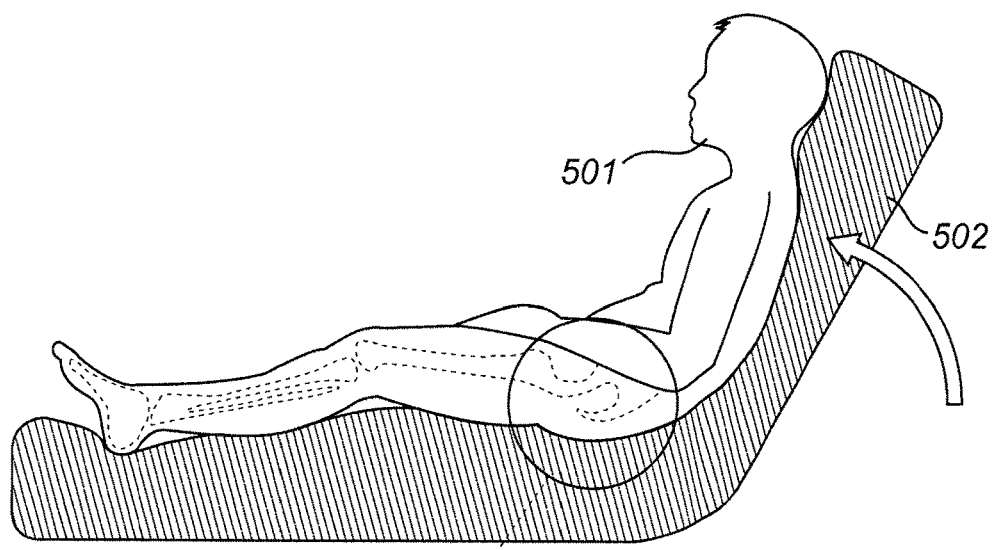
FIG. 5a illustrates a bedridden patient exposed to pressure and shear forces when the head of the bed is tilted upwards when no dressing is used.
Figure 5B:
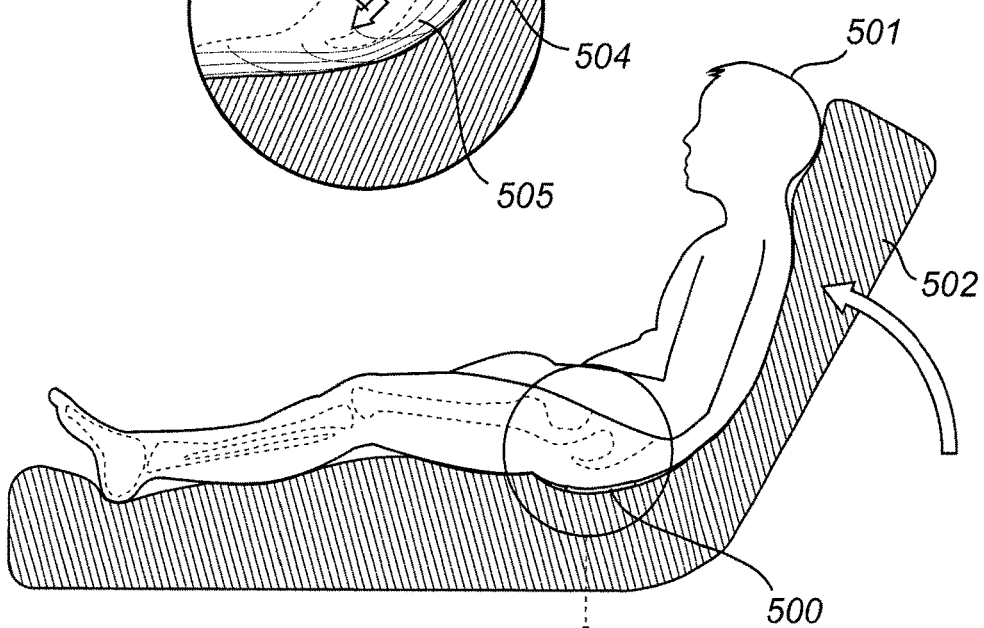
FIG. 5b illustrates a bedridden patient exposed to pressure and shear forces when the head of the bed is tilted upwards when a dressing of the invention has been applied to the sacrum region of the patient.

FIGS. 5a-5b illustrate a patient 501 positioned in an adjustable bed 502, where the head of the bed has been elevated and the patient 501 has been placed in a more upright condition. When no dressing is used (FIG. 5a), the patient 501 is subject to pressure compressing the tissue, and to shear forces 503 distorting or deforming the soft tissue layers 504. The individual tissue cells 505 are thus subject to both pressure and compression, and also to shear forces 503 that arise from the patient 501 sliding in bed 502. This has a negative impact on the soft tissue, and the tissue cells 505 are more prone to deformation, which ultimately may lead to the formation of a pressure ulcer.

In FIG. 5b, a dressing 500 according to the present invention has been applied to the sacrum region of the patient 501 such that the stiff, second direction (y) corresponds to the direction of which the tissue is exposed to most shear and stretch (i.e. the sliding direction of a patient). When a dressing is applied to the sacrum region, the pressure forces are reduced by the dressing 500 and distributed over a larger area. This leads to pressure re-distribution and reduced magnitude of critical forces on the skin and underlying tissues. The shear forces 503 are reduced by the dressing 500 since the dressing is stiff in the direction in which the patient 501 slides in bed 502. Therefore, the stiff dressing 500 "locks" the skin and underlying tissues such that they do not stretch excessively in the region where the dressing 500 is applied. The fact that the dressing is flexible in the first direction (x) is advantageous since it prevents the tissues from becoming "over constrained". Instead, the sacral buttocks can spread gently and naturally. The individual tissue cells 505 in the sacral region of the patient 501 are therefore maintained relatively intact. The stretching of the skin may still occur at skin areas outside the dressing (which areas are at less risk for pressure ulcer formation caused by deformation, pressure and shear). This way, pressure forces, shear forces and the stress and stretch on skin cells and the underlying tissue cells are minimized.

Figure 6:
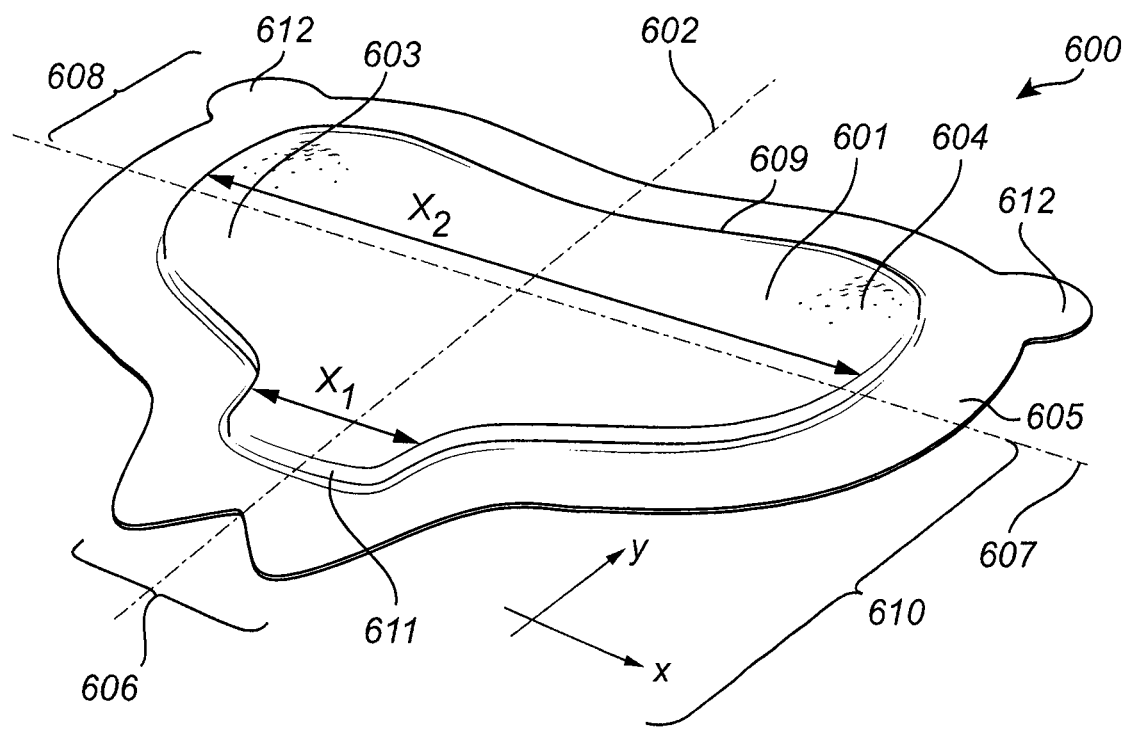
FIG. 6 illustrates an exemplary embodiment of the dressing according to the invention.

An exemplary embodiment of this aspect of the present invention is illustrated in FIG. 6. The shape of the dressing is suitable for application to the sacrum area of a patient.

The medical dressing 600 has a lateral (x) extension and a longitudinal (y) extension; the pad 601 being symmetric about a longitudinal center line 602 and the dressing comprising a first lobed portion 603 on one side of the longitudinal center line 602 and a second lobed portion 604 on the other side of the longitudinal center line 602.

The anisotropic layer (not shown) is arranged such that the first direction (x) of the anisotropic layer corresponds to the lateral (x) extension of the dressing 600, and the second direction (y) of the anisotropic layer corresponds to the longitudinal extension of the dressing 600. Hence, the dressing is stiffer in the longitudinal (y) direction than in the lateral (x) direction.

The border portion 605 may be substantially heart shaped such that the first 603 and second 604 lobed portions form part of the lobed upper sides of a heart shape. Suitably, the first and second lobed portions are separated by a forked portion 606 which replaces the pointed lower part of a heart shape. The forked portion 606 comprises a protrusion on either side of an interstice located coaxially with the longitudinal center line.

The shape of the medical dressing 600 is adapted to fit to the sacral region of a human body. The forked portion 606 allows for an improved stay-on ability in the gluteal cleft region. It is important that the dressing remains adhered in this region since otherwise body fluids (for example as a result of incontinence) may enter into the dressing and impair the adhesion to the skin.

The coccyx is an area exposed to a large amount of pressure and shear. It is therefore important to protect this part of the body, and the dressing suitably has a shape that allows for such protection.

Hence, the pad 601 may be divided by a lateral center line 607 into an upper pad region 608 having an upper lateral edge 609 and a lower pad region 610 having a lower lateral edge 611. The width, $x_1$, of the lower lateral edge 611 is between 10 and 40% of the maximum width, $x_2$, of the pad 601 in the lateral (x) direction.

The maximum width, $x_2$, of the pad of the dressing 600 is typically in the range of from 12 to 30 cm, preferably from 15-20 cm. The width, $x_1$, of the lower lateral edge may be in the range of from 1 to 7 cm, e.g. from 2 to 4 cm, depending on the size of the dressing.

In embodiments, the dressing 600 comprises at least one gripping tab 612; the gripping tab 612 being coplanar with and projecting outwardly from the periphery of the dressing 600.

The gripping tab 612 guides the caregiver to lift the dressing, inspect the skin underneath the dressing, and to thereafter re-apply the dressing onto the skin (in case the skin looks ok). Inspection of skin may still be required, albeit on a less frequent basis when the dressing is transparent. Since the inspection of the skin typically takes place where the patient is lying on the side in the bed, it is beneficial to have at least two gripping tabs such that the caregiver can lift the dressing regardless of which side the patient lies. In FIG. 6, the gripping tab 612 is coplanar with and projects outwardly from the border portion of one of the lobed portions 603 and 604.

Figure 7:
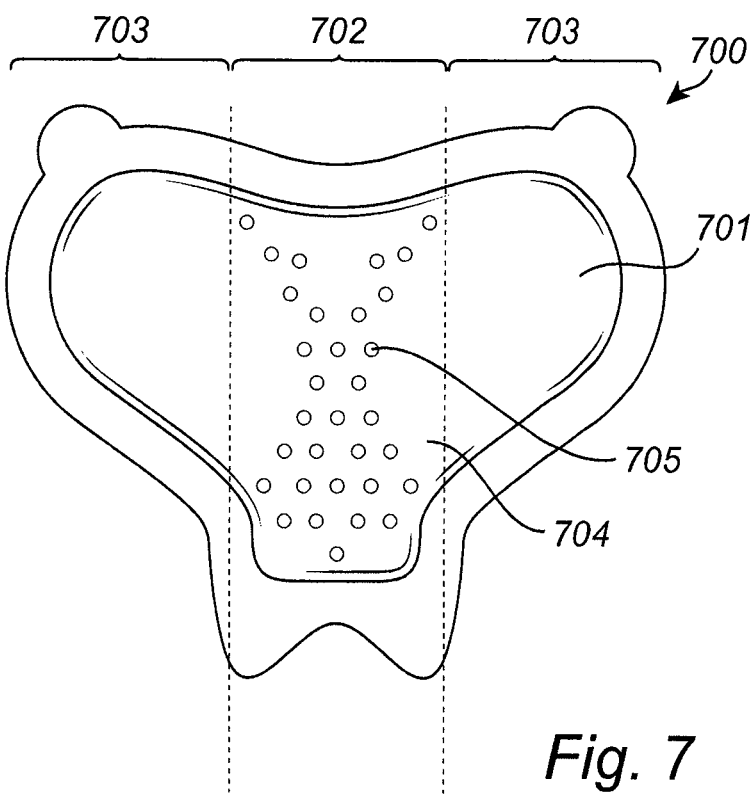
FIG. 7 illustrates a dressing according to an exemplary embodiment comprising three lateral pad zones, wherein the central zone comprises indentations in the form of apertures.

As illustrated in FIG. 7, the pad 701 may be divided into three separate zones along the longitudinal (y) extension of the dressing 700: one central zone 702 and two lateral zones 703.

The central zone 702 of the dressing 700 is the area exposed to most pressure and shear stresses, especially in the lower part 704 of the central zone 702 which is arranged to cover the coccyx region of a patient. In the embodiment envisioned in FIG. 7, the gel pad comprises a plurality of indentations 705 in at least the central zone 702.

As used herein, the term "indentations" means areas of reduced pad thickness. The indentations may be apertures that extend through the gel pad.

The indentations 705 allow for a localized softening of the gel pad while preserving the overall properties of the gel dressing. The inventors have found that the skin and the soft tissue underneath is better protected by the provision of indentations 705 in the central zone.

In embodiments, the pad 701 may be divided into three separate zones along the longitudinal (y) extension of the dressing 700: one central zone 702 and two lateral zones 703, wherein the compressive strength of the gel in the central zone 702 is lower than in the lateral zones.

Accordingly, the dressing may be formed of different regions having different properties; i.e. compressive strengths. The inventors have found that the central zone 702 may be softer, i.e. have a lower compressive strength to prevent the soft tissue cells from becoming deformed and damaged. In embodiments, the central dressing zone 702 may have a compressive strength in the range specified above, and the lateral zones 703 of the dressing may have a higher compressive strength.

In another aspect, the invention relates to a dressing as described hereinbefore for use in the prevention of pressure ulcers.

However, although the primary use of the invention is for prevention, such a dressing may also be used in the treatment of pressure ulcers or wounds, especially low exuding wounds.

Although the dressing of the present invention is primarily directed for prophylactic use, it is preferred that the dressing has sufficient absorbency, as shown in the Example section below. A prophylactic dressing needs to be able to handle low exuding wounds and body fluids such as sweat, small amounts of blood, and pus.

EXAMPLES

Preparation of Gels According to the Invention
Gel A 23 g 4-hydroxybutylacrylate, 3 g AMPS, 0.02 g PEG400 diacrylate (from Sartomer), 50 g glycerol, 30 g PEG400 (from Sigma-Aldrich), and 0.15 mg Omnirad 1000 (from IGM Resins) were placed in a speed mixer jar, wherein the UV initiator Omnirad was added last into the mixture. The ingredients were then mixed in the speed mixer for 2 minutes at 2400 rpm.

After mixing, the jars were left to rest for at least 3 hours in a dark box, in order get rid of air bubbles from the gel solution.

Thin gels (up to 5 mm) were then cured for 20 seconds in UV light, for absorption and opacity measurements. Thicker gels (25 mm) were cured for 1 minute in UV light for compression test and analysis of the compressive strength.

The water content of gel A was 9% by weight.

Gel B 29.75 g MPEG450A (from Sigma Aldrich), 0.25 g PEG400diA (from Sartomer), 70 g Glycerol/urea (70/30 mix) and 0.1 Omnirad 1000 (from IGM Resins) were placed in a speed mixer jar, where in the UV initiator Omnirad was added last into the mixture. The ingredients were then mixed in the speed mixer for 2 minutes at 2400 rpm.

After mixing, the jars were left to rest for at least 3 hours in a dark box, in order get rid of air bubbles from the gel solution.

Thin gels (up to 5 mm) were then cured for 20 seconds in UV light, for absorption and opacity measurements. Thicker gels (25 mm) were cured for 1 minute in UV light for compression test and analysis of the compressive strength.

The water content of gel B was 4% by weight.

Absorption Capacity of the Gels

To analyze the absorption capacity on the gels, Solution A (according to EN 13726-1:2002) diluted with distilled water in a ratio of 1:5 was used. The dry weight of the gels was noted. Gels were left to absorb liquid from a wet surface without being plunged into the liquid in room temperature. The surface used was Mesorb®, cut to approximately the same size as the gels (1-2 mm excess material on each side, due to swelling of the gel). The Mesorb® pieces were soaked with 20 ml of liquid (this is how much the piece could retain), and the gel was placed on top of that. A beaker was covered with Parafilm® to prevent evaporation of liquid. After four hours, an additional 10 ml of liquid was added to the Mesorb® piece to make sure it stayed saturated. The setup was then left for another 18 hours. In total, the gels were left to absorb liquid for 22 hours. After the swelling, the weight of the gels was noted again.

Opacity of the Gels (Determined in Accordance with Standard ASTM 2244-11)

After the gels had been wetted and swollen, the opacity was measured with a Minolta Chroma Meter CR 300 according to ASTM D2244-11 to study the opacity after liquid exposure.

The method measures Yxy color space values on specimens that can be used to calculate the opacity number.

Apparatuses: Chroma meter CR-300 and Data processor DP-301.

Sample preparation: The specimen with an initial height of 4 mm is allowed to absorb liquid according to the method described above.

Procedure: Yxy color space values are measured on the wet test specimens. The Chroma meter is calibrated according to the apparatus instructions. The apparatus is set to measure color space values. The specimens are first placed on a black background and the tip of the measuring head is placed flat against the specimen surface. When the measuring head's lamp is light the measuring button is pressed. 5 measurements are taken on each specimen. The specimens are then moved to a white background and the tip of the measuring head is placed flat against the specimen surface. 5 measurements are taken on each specimen.

The following results are measured in the method:

Y x y color space values

Opacity number, $Y_{black}/Y_{white}$ (expressed as %)

Compressive Strength of the Gels (Determined in Accordance with Standard ASTM D3574-11, Test C)

Apparatus: MTS insight
Tensile tester connected to a computer
Crosshead speed: 50 mm/min
Plate distance: 37.5 cm Sample preparation: The area of the specimen should be at least 2500 mm$^2$ (50 mm*50 mm) with a height of at least 20 mm, preferably 25 mm. The samples are conditioned for 24 h in 50 percent RH plus or minus 5 percent RH and 23 degrees centigrade plus or minus 2 degrees centigrade before testing.

Procedure: The tensile tester is calibrated according to the apparatus instructions and set to zero. The distance between the upper and lower plate is set to 37.5 mm. The specimen is centered on the supporting plate of the apparatus. The compression foot goes down and the thickness at 140 Pa is determined. The specimen is compressed 50% of this thickness at a speed of 50 mm/min and then the upper plate goes directly back up.

The following results are expressed by the tensile tester/computer:

Load [N]

Specimen thickness at 140 Pa [mm]

Young's modulus at 20% strain and 50% strain [kPa]

The compressive strength is calculated by dividing the load at specific strains, by the original cross-sectional area of a specimen. The compressive strength as defined here is independent of the maximum compressive strength before fracture (i.e. the maximal stress that a material can take in before it breaks).

The results from absorption, opacity and compressive strength tests for gels of the present invention and commercially available gels as used in pads for medical uses are summarized in the table below.

TABLE 1

Characteristics of inventive and commercially available gels

| Gel mixture | Compressive strength at 50% strain | Compressive strength at 25% strain | Absorption capacity (%) | Opacity (%) |
| --- | --- | --- | --- | --- |
| Gel mixture A | 13.0 | 2.9 | 36.8 | 12.2 |
| Gel mixture B | 15.0 | 2.8 | 84.1 | 9.8 |
| KerraPro ® | 83.5 (45% strain*) | 23.8 | 0 | 29% |
| Elasto-Gel ™ | 64.6 | 14.8 | N/A | N/A |

*Measured at 45% strain since the limit of the load cell (250 N) was reached before 50% strain (since the gel was so stiff).

Tensile Force (Determined in Accordance with Standard: ASTM D882-12)

Apparatus: Tensile tester for e.g. MTS insight
Tensile tester connected to a computer
Crosshead speed: 50 mm/min
Grip separation: 100 mm Sample preparation: Test specimens are punched from the material. The width of the specimens is 25 mm and the length at least 50 mm longer than the grip separation if possible. It is of importance that the edges of the specimens are even and without break notches. The specimens are conditioned for at least 24 h in 50 percent RH plus or minus 5 percent RH and 23 degrees centigrade plus or minus 2 degrees centigrade before testing.

Procedure: The tensile tester is calibrated according to the apparatus instructions and set to zero. The sample is then mounted in the clamps and slack and pre-tension should be minimized. The tensile tester is started and the sample is elongated until break or until reaching 100% elongation, the tensile force (load) versus elongation is recorded. Measurements resulting from premature failures (i.e. the sample breaks at the clamp, or is damaged during preparation) are ignored if possible.

The following results are expressed by the tensile tester/computer:

Strain [%], extension/gage length
Load at specific strain (e.g. at 15% strain)

Figure 8A:
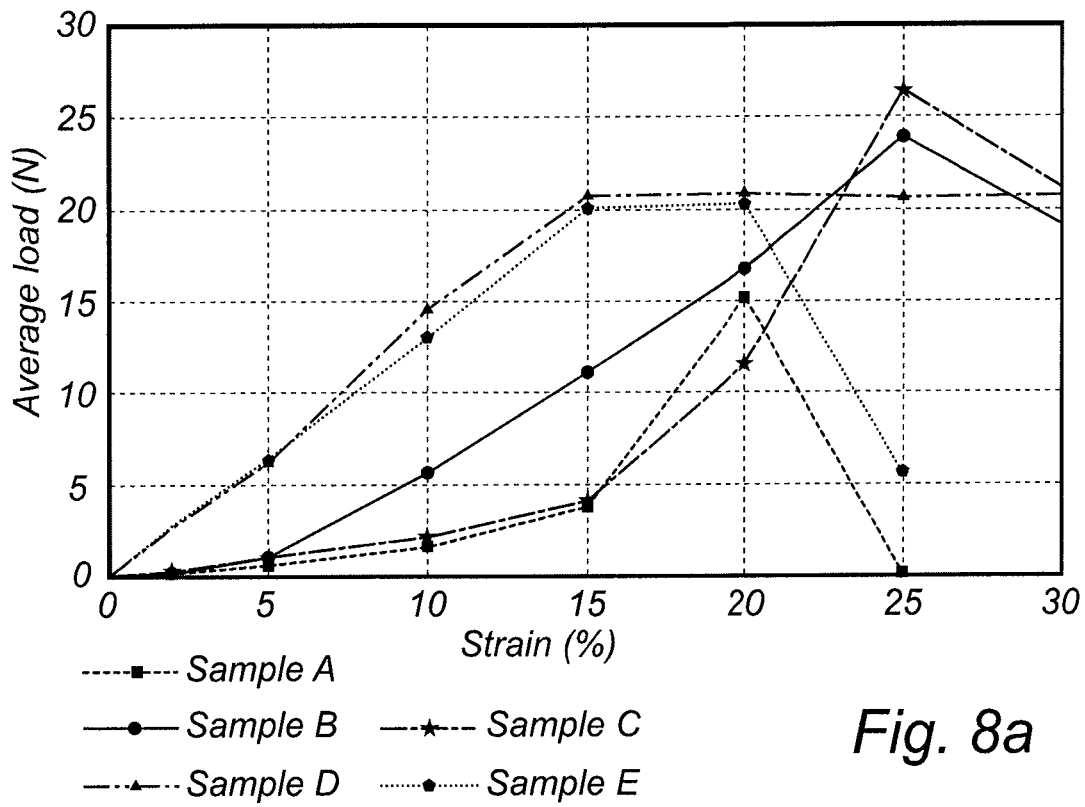
FIG. 8a illustrates the tensile curves for five different types of anisotropic layers in the second direction (y).
Figure 8B:
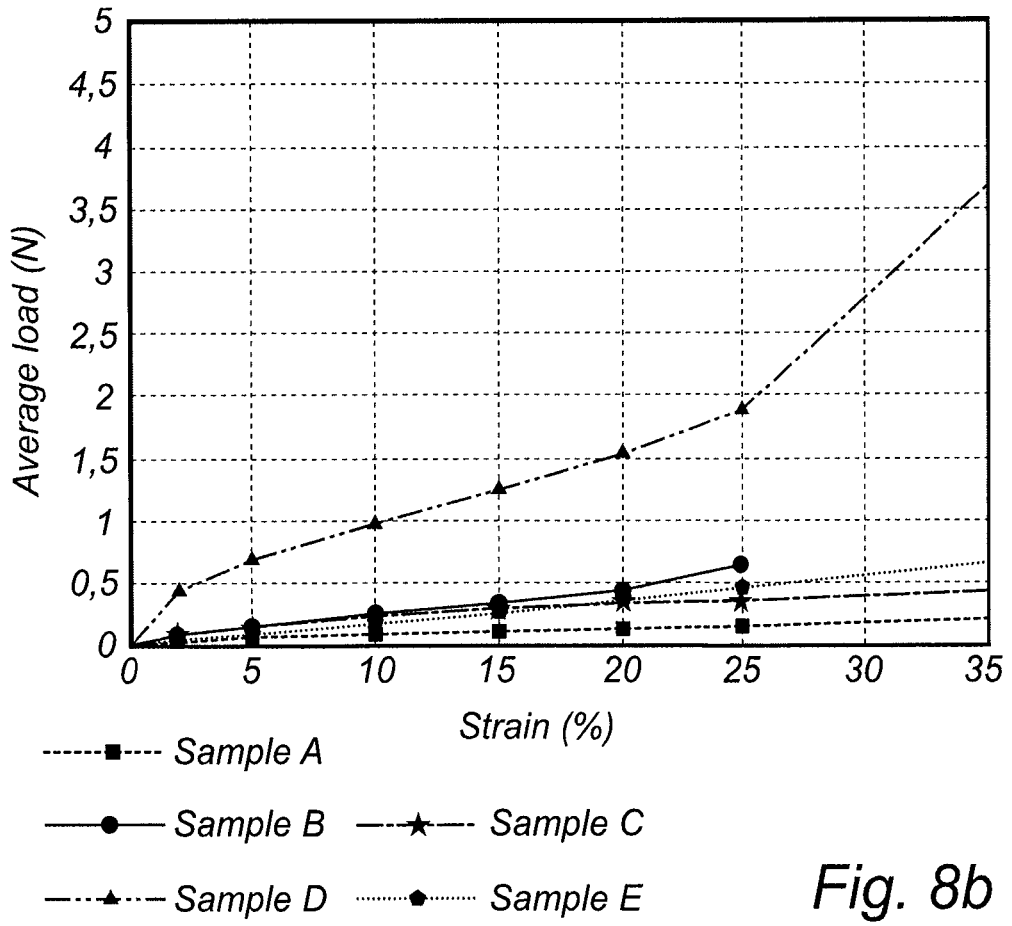
FIG. 8b illustrates the tensile curves for five different types of anisotropic layers in the first direction (x).

Five different anisotropic layers were tested, and their tensile curves are illustrated in FIGS. 8a-8b. FIG. 8a illustrates the tensile curves in the second direction (y) and FIG. 8b illustrates the tensile curves in the first direction (x). Sample A was M33116-A (polyamide) from Eschler, sample B was M33116-B (polyamide) from Eschler, sample C was 322223 (polyester) from Eschler, sample D was 114160 Delstar (polyamide sample) from DEKA Medical, and sample E was a 40 gsm spunlace nonwoven comprising viscose and polyethylene (70:30).

Finite Element (FE) Modelling

The mechanisms leading to pressure ulcers are not fully understood. Pressure sensing mats can give information on pressure present at the mattress under the skin surface but does not inform on the behaviour inside the soft tissues, at the origin of damage. Therefore, the Finite Element (FE) method offers a great alternative to study the biomechanisms of action for pressure ulcers.

The FE method is a numerical and computational technique used to solve multiphysics problems by solving partial differential equations upon different types of discretizations. The FE method subdivides a large problem or large 3D model into smaller parts called finite elements. The analyses are performed within each elements and the assembly gives a solution to the entire problem.

The workflow for a FE analysis can be explained as follows: creation of a 3D model constituted of finite elements, definition of the material properties of the model, definition of the boundary conditions and loadings to apply to the model according to the problem, computational solving of the problem, and analysis of the results through visualization and calculations.

Finite Element (FE) Settings and Anatomical Model

In order to understand the effect of the dressing according to the present invention, finite Element (FE) models of a pelvis and of a dressing according to the invention were created and analyses were performed to study the effect of pressure and stresses on the skin and in deep tissue layers. The volunteer was a non-smoker healthy adult male of 31 years at the time of the study (year birth 1984, length: 183 cm, weight: 77 kg).

The FE models were prepared in prepared in ANSA 16.0.1 and 17.1.0 (BETA CAE) and the analysis performed in ABAQUS 14.0 (DASSAULT SYSTEM). The FE model of the pelvis was segmented from MRI scans of the pelvis in order to insure the best anatomical accuracy.

The soft tissues were represented as non-linear materials (the muscles were lumped together as one material, the fat and the skin were lumped together as one compressive material), the bones as rigid body. The deformation of the soft tissue caused by compression from the body weight was used to validate the FE model and its material properties with ABAQUS 14.0 (DASSAULT SYSTEM). The validation was carried out by comparing the thickness of the soft tissues before and after compression between the model and the MRI data.

The deformation of the soft tissue was performed by simulating a clinical setting where a patient is lying on a mattress. A soft mattress (30 kPa) was added under the pelvis and the equivalent of the body weight was applied to induce contact and compression of the pelvis on the mattress.

The deformation of the soft tissue due to pure compression was simulated with a vertical displacement of the body on mattress, while the additional effect of the shear force was induced by a following horizontal displacement of the body on the mattress to mimic elevated position.

The following soft tissue layers were investigated for stress distribution, and the following stresses were analysed:

TABLE 2

Soft tissue layers and simulated stresses

| Soft tissue layer | Definition of soft tissue layer | Stresses in compression | Stresses in compression + shear |
|---|---|---|---|
| At the skin | Posterior part of the skin/fat lump | Mean pressure | Mean pressure |
| At the muscle | Posterior part of the muscle, interface between the muscle and the fat | Von Mises stresses, VMS | Von Mises stresses, VMS |
| At the muscle next to the bones | Anterior part of the muscle, focus on the sacrum area, interface between the muscles and the sacrum bones. | | Shear stresses |

"Stresses in compression" means the stresses that arise from compression; i.e. defined as the vertical displacement of the body on a mattress to mimic the compression of the pelvis when the patient is lying horizontally on a mattress.

"Stress in compression+shear" means the stresses that arise from added shear after compression; i.e. defined as the horizontal displacement of the body on a mattress to mimic the sliding of the pelvis after compression when the patient is lying on an inclined mattress.

The mean pressure (or hydrostatic stress) and the Von Mises stresses give an overview of the strain energy density and help to capture the origins of the strains and stresses in the tissues.

"Shear stresses" means stresses in the plane, parallel to the coronal plane or dressing plane, and due to the shear forces that apply to the cross section area parallel to the direction of the force The Von Mises Stresses (VMS) are defined in the Distorsion Energy Theory and represent a common criterion widely used in engineering. The VMS can be defined as:

$$\sigma_{VM} = \sqrt{\frac{1}{2}\left[(\sigma_{xx}-\sigma_{yy})^2 + (\sigma_{yy}-\sigma_{zz})^2 + (\sigma_{zz}-\sigma_{xx})^2\right] + 3\left(\tau_{xy}^2 + \tau_{yz}^2 + \tau_{zx}^2\right)}$$

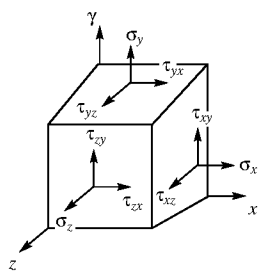

The Mean Pressure (or hydrostatic stress) can be defined as:

$$\sigma Hyd = \tfrac{1}{3}(\sigma xx + \sigma yy + \sigma zz)$$

The strain energy density is separated into different components in order to isolate the hydrostatic stresses and the deviatoric stresses. The deviatoric stresses are represented by the VMS and combine stresses in different directions into an equivalent stress that will take into account normal stresses, shear stresses and distortion. Combined with the hydrostatic stresses, the VMS can give an overview of the separate components of the strain energy density and help to capture the origins of the strains and stresses in the tissues.

The physical and mathematical relationship between force, stress, displacement and strain are the following:

Strain ε is defined as "deformation of a solid due to stress" and can be expressed as:

$$\varepsilon = dl/L_o$$

wherein
dl=change of length or displacement (mm)
$L_o$=initial length (mm)

The Young's modulus E (MPa) is a property of the material and can be defined as:

$$E = \sigma/\varepsilon$$

Shear stresses are stresses parallel to the plane and can be expressed as:

$$\tau = F_p/A$$

wherein
τ=shear stress (MPa)
$F_p$=parallel component force (N)
A=area (mm²)

There are no known values of critical stresses, as it varies between individuals, due to their physiological parameters, health, age and with the duration of exposure to the stresses. Therefore, the evaluation of the effect of the dressings relies on qualitative values. In the FIGS. 9a-14c, the black areas show higher stresses (critical values of stresses). Critical values of stresses have been defined as high value of stresses showing difference with "no dressing" and the dressings.

The critical value of stresses correspond to about 1 kg for 10 cm² (around 10 kPa), except for the shear stresses, where a lower value of the critical stresses was used, corresponding to about 100 g for 10 cm² (around 1 kPa), as the stresses are applied parallel to the muscle fibers and therefore against a more natural compressive behaviour.

Effect of Inventive Gel Dressing

A dressing with the properties according to the invention (low compressive strength) was created from technical CAD drawings and was designed to match the properties of the dressing as defined in claim 1. The compressive strength of the gel at 25% strain was 4.2 kPa, and the Youngs modulus, E, was 0.008 MPa. The inventive dressing is denoted "Dressing A".

For comparative purposes, a more rigid gel, in accordance with prior art was designed and inserted into the model. This dressing is referred to as "Dressing B". Dressing B had gel pad with a compressive strength at 25% strain of 14.6 kPa, and a Young's modulus, E, 0.03 MPa, corresponding to the properties of the Elastogel® dressing.

The rest of the components and properties of dressing A and B were identical in the simulations; i.e. they had identical shapes, and both comprised a simulated backing layer and a border portion surrounding the gel pad. In the simulations, the skin-facing surface of the dressings was fully adherent to the skin. For all dressings, the gel pad material was considered as linear elastic isotropic material and nearly incompressible.

The material properties of the different dressings were defined by actual laboratory measurements in tension and compression based on ASTM D 882-12 and ASTM D 3574-11.

Simulations were performed to analyse the stresses in compression and in compression+shear. The simulated model was wearing: no dressing, dressing A and dressing B, respectively.

Figure 9A:
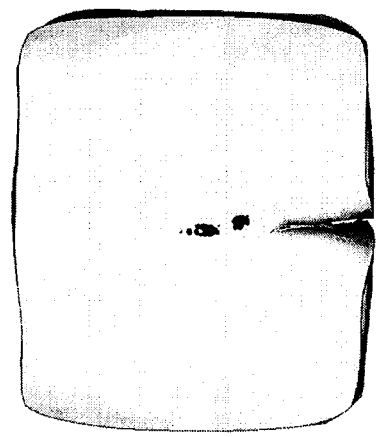
FIG. 9a illustrates the mean pressure (hydrostatic stress) distribution at the skin arising from compression in a Finite element (FE) model simulation, when no dressing is used.
Figure 9B:
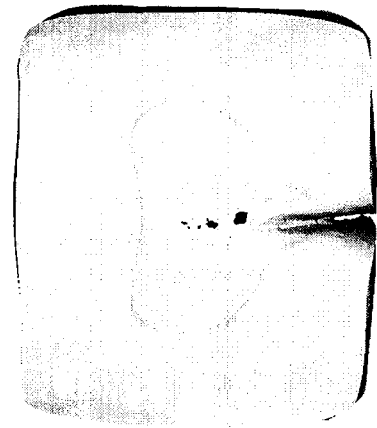
FIG. 9b illustrates the mean pressure (hydrostatic stress) distribution at the skin arising from compression in a Finite element (FE) model simulation, when a dressing comprising a more rigid gel according to prior art is used.
Figure 9C:
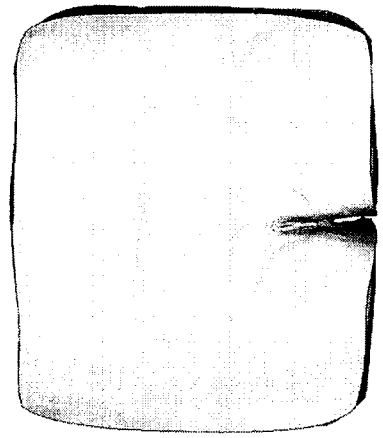
FIG. 9c illustrates the mean pressure (hydrostatic stress) distribution at the skin arising from compression in a Finite element (FE) model simulation, when a dressing according to an exemplary embodiment of the present invention is used.
Figure 10A:
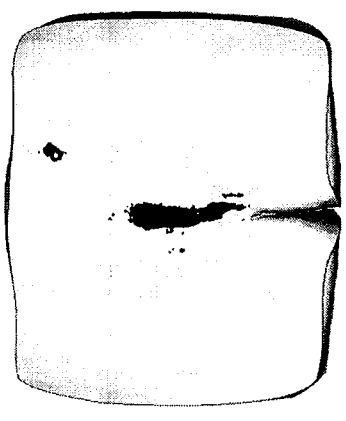
FIG. 10a illustrates the mean pressure (hydrostatic stress) distribution at the skin arising from compression and shear in a Finite element (FE) model simulation, when no dressing is used.
Figure 10B:
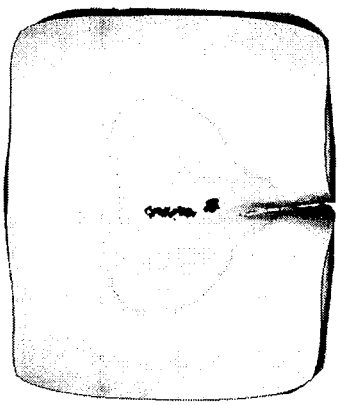
FIG. 10b illustrates the mean pressure (hydrostatic stress) distribution at the skin arising from compression and shear in a Finite element (FE) model simulation, when a dressing comprising a more rigid gel according to prior art is used.
Figure 10C:
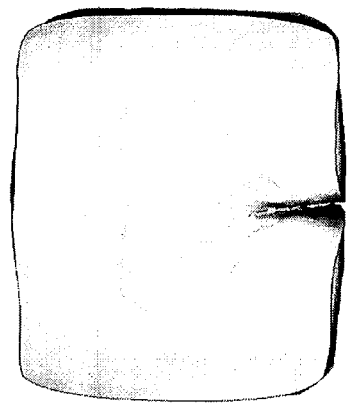
FIG. 10c illustrates the mean pressure (hydrostatic stress) distribution at the skin arising from compression and shear in a Finite element (FE) model simulation, when a dressing according to an exemplary embodiment of the present invention is used.

FIGS. 9a-9c and 10a-10c illustrate the mean pressure at the skin in the sacrum region after exposure to pressure and compression (FIGS. 9a-9c) and when shear has been added; i.e. the patient has been subject to both compression and shear (FIGS. 10a-10c). The black spots in FIGS. 9a-9c and 10a-10c show the areas exposed to critical pressure. The critical value of stresses correspond to about 1 kg for 10 cm² (around 10 kPa).

As can be seen, in FIG. 9c, the inventive dressing dramatically decreases the critical compression stresses at the skin compared to when no dressing is used (FIG. 9a) and when a more rigid dressing is used (FIG. 9b). In fact, when a dressing according to the invention is applied, there are no critical stresses present on the skin.

FIGS. 10a-10c illustrate the mean pressure at the skin in the sacrum region, when shear has been added, simulating e.g. a patient sliding in bed. As can be seen in FIG. 10c, the inventive dressing removes all critical stress compared to when no dressing is used (FIG. 10a) or when a dressing in accordance with prior art is used (FIG. 10b).

One way to evaluate the performance of the dressings is to define its ability to reduce the volume of tissue under critical stresses. Critical values of stresses are defined as high value of stresses showing difference with "no dressing" and the dressings. As mentioned, for the Von Mises Stresses, the critical value of stresses correspond to about 1 kg for 10 cm² (around 10 kPa).

The performance of the dressing can therefore be defined as the percentage reduction of volume of tissue under critical stress when compared to no dressing:

$$\text{Reduction (\%)} = \frac{(V_{nd} - V_d)}{V_{nd}} \times 100$$

with Reduction (%)=percentage reduction of volume of tissue under critical stress
with $V_{nd}$=Volume of tissue under critical stress with no dressing
with $V_d$=Volume of tissue under critical stress with dressing The Von Mises stresses inside the soft tissue (muscles) of the sacral area under the dressing was analysed and compared between No dressing, dressing A and dressing B. The table below summarizes the volume of soft tissue subject to critical stresses. Although already illustrated in FIGS. 9a-9c and 10a-10c, the reduction of volume of skin under critical mean pressure is also included in Table 3 below.

TABLE 3

Percentage reduction of volume of muscle and skin under critical VMS stress

|  | Compression only | | Compression + shear | |
| --- | --- | --- | --- | --- |
| Critical stresses studied in FE | Dressing A | Dressing B | Dressing A | Dressing B |
| Reduction of volume of muscle under critical VMS stress | 46% | No reduction - 66% increase | 77% | 60% |
| Reduction of volume of skin under critical mean pressure | 100% | 74% | 100% | 63% |

The volume of muscle under critical VMS stress was substantially reduced when a dressing of the present invention was used. Remarkably, the critical VMS stresses actually increased with the prior art dressing (Dressing B); i.e. the dressing created more stresses in the tissue compared to when no dressing was used.

Effect of Gel Dressing with Support Layer

The effect of the incorporation of an anisotropic layer was also studied. A simulated anisotropic layer in accordance with sample E above was inserted into the dressing concept. The simulated anisotropic layer refers to a shell with properties similar to a layer having a tensile force at 15% strain of 20.6 N in the second direction (y), and 0.3 N in the first direction (x). This dressing concept is referred to as Dressing C.

Figure 11A:
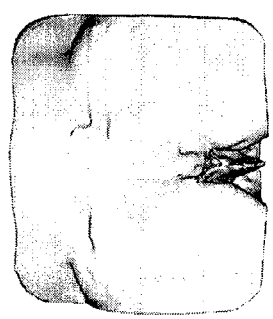
FIG. 11a illustrates the Von Mises stress distribution at the muscle arising from compression and shear in a Finite element (FE) model simulation, when no dressing is used.
Figure 11B:
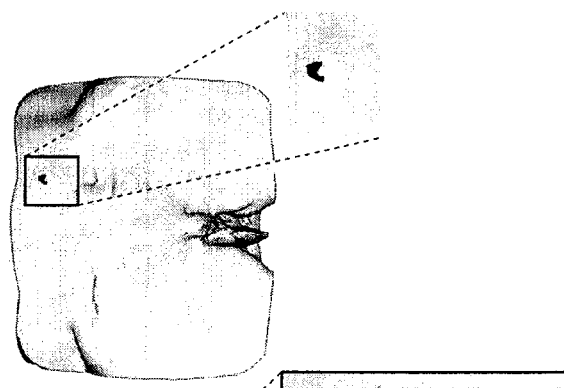
FIG. 11b illustrates the Von Mises stress distribution at the muscle arising from compression and shear in a Finite element (FE) model simulation, when a dressing comprising a more rigid gel according to prior art is used.
Figure 11C:
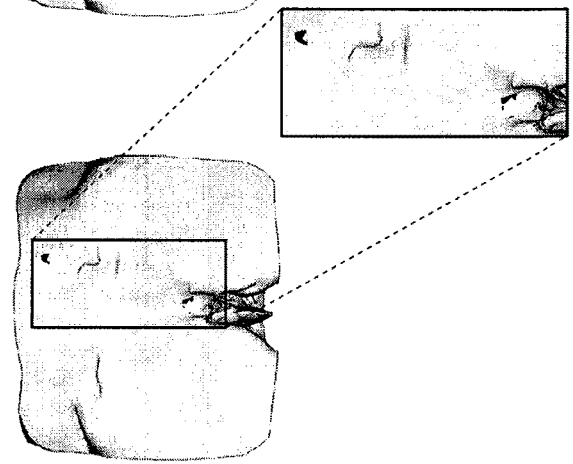
FIG. 11c illustrates the Von Mises stress distribution at the muscle arising from compression and shear in a Finite element (FE) model simulation, when two dressings according to exemplary embodiments of the present invention are used.
Figure 11D:
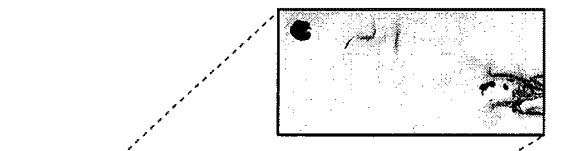
FIG. 11d illustrates the Von Mises stress distribution at the muscle arising from compression and shear in a Finite element (FE) model simulation, when two dressings according to exemplary embodiments of the present invention are used.
Figure 15:
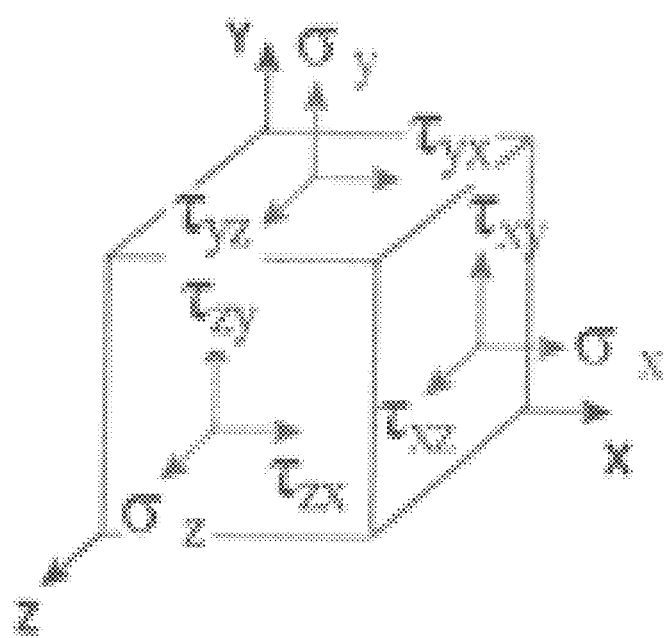
FIG. 15 is a schematic illustrating the orientation in space of the variables used to calculate the Von Mises stresses.

In FIGS. 11a-11d, the Von Mises stresses at the muscle when the model has been subject to compression and shear, are presented. FIG. 11a illustrates the situation when no dressing is used, FIG. 11b illustrates Dressing B, FIG. 11c illustrates Dressing A, and FIG. 11d illustrates Dressing C, i.e. Dressing A with an anisotropic layer.

As can be seen, the VMS stresses at the muscle are substantially reduced with the inventive Dressing A (FIG. 11c), and nearly all stresses are removed in the coccyx region. Dressing C completely reduces the VMS stresses across the sacral area (FIG. 11d), and it can be concluded that the anisotropic layer is particularly beneficial when the body is exposed to shear; resulting e.g. from patient sliding.

The results are also presented in Table 4 below in terms of the ability of the dressings to reduce the volume of tissue under critical stresses for a simulated compression+shear set-up (reflecting the results of FIGS. 11a-11d).

TABLE 4

Percentage reduction of volume of muscle under critical VMS stress with inventive dressings A and C

|  | Compression + shear | |
| --- | --- | --- |
| Critical stress studied in FE | Dressing A compared to no dressing | Dressing C compared to no dressing |
| % reduction of volume of muscle under critical VMS stress | 77 | 100 |

The shear at the muscle next to the bones was also studied. Shear stresses occur in the tissue in numerous settings, and they are due to shear forces, that have been identified as one of the major causes of pressure ulcers. For the shear stresses, the critical value of stresses correspond to about 100 g for 10 cm$^2$ (around 1 kPa), as the stresses are applied parallel to the muscles fibers and therefore against a more "natural" compressive behaviour.

FIGS. 12a-12c illustrates the effect of the inventive dressings A (FIG. 12b) and C (FIG. 12c) with respect to reducing shear stresses at the muscle next to the bones in the sacrum area, compared to when no dressing is used (FIG. 12a).

As illustrated in FIG. 12b, the inventive Dressing A substantially reduces the harmful shear stresses, and the reduction of volume under critical shear stresses was calculated to be 91%. Notably, the inventive Dressing C completely removed the critical shear stresses at the muscles next to the sacral bone (FIG. 12c), and the calculated reduction of volume under critical shear stresses was 100%. This clearly illustrate the effect of the gel, and particularly the positive effect of an anisotropic layer when subject to harmful shear forces.

Effect of Gel Dressing Having Apertures and/or a Lower Compressive Strength in the Central Zone Two additional inventive dressing concepts were investigated; i.e. Dressing D and Dressing E. Dressing D, illustrated in FIG. 13a was similar to Dressing C in construction, but further comprised apertures in the central zone of the pad (both through the pad and through the anisotropic layer). Dressing E, illustrated in FIG. 13b, was similar in construction as Dressing D, but further comprised a region in the central zone of the dressing (near the coccyx) with a lower compressive strength; namely 3.1 kPa at 25% strain. The remaining pad had a compressive strength in accordance with the other dressing concepts (4.2 kPa at 25% strain).

The ability of the dressings to reduce the volume of tissue under critical stresses, in a simulated compression set-up was studied, and the results are presented below.

TABLE 5

Percentage reduction of volume of muscle under critical VMS stress with inventive dressings A, D and E

|  | Compression only | | |
| --- | --- | --- | --- |
| Critical stress studied in FE | Dressing A compared to no dressing | Dressing D compared to no dressing | Dressing E compared to no dressing |
| % reduction of volume of muscle under critical VMS stress | 24% | 64% | 92% |

The effect of the inventive dressings D and E are also illustrated in FIGS. 14a-14c, which shows the Von Mises stresses at the muscle in simulated compression conditions for a pelvis without any dressing (FIG. 14a), a pelvis when Dressing D has been applied (FIG. 14b) and a pelvis when Dressing E has been used (FIG. 14c). In other words, FIGS. 14a-14c illustrate the effect on the soft tissue (muscles) after exposure to pressure and compression.

As can be seen, the provision of apertures and/or a pad region having a lower compressive strength substantially reduce the critical stress areas (black spots).

Other embodiments of the invention will be apparent to those skilled in the art from consideration of the specification or practice of the invention disclosed herein. It is intended that the specification and examples be considered as exemplary only, with the true scope of the invention being indicated by the following claims.

The invention claimed is:

1. A medical dressing configured to be applied on intact skin and configured to prevent an onset of a pressure ulcer during use, wherein the medical dressing has a first side and a second opposing side, wherein the first side has a skin-facing surface adapted to detachably adhere the medical dressing to a dermal surface; the medical dressing comprising a gel pad arranged between a backing layer and an adhesive body contact layer, wherein the adhesive body contact layer comprises the skin-facing surface of the first side, wherein the adhesive body contact layer comprises a silicone based adhesive,
wherein at least the backing layer extends beyond the periphery of the gel pad to define a border portion around a contour of the gel pad,
wherein a gel of the gel pad has a compressive strength of from 5 to 60 kPa at a strain of 50%, as measured according to a compression test, wherein the gel pad is configured to prevent the onset of the pressure ulcer during use,
wherein the gel pad, the backing layer, and the adhesive body contact layer are substantially transparent,
wherein the substantial transparency of the gel pad, the backing layer, and the adhesive body contact layer in combination with the compressive strength of the gel of the gel pad allows a caregiver to perform a blanching test through the medical dressing of an area of a subject covered by the gel pad, the backing layer, and the adhesive body contact layer during use.

2. The medical dressing configured to be applied on intact skin and configured to prevent an onset of a pressure ulcer during use according to claim 1, wherein the medical dressing has a lateral (x) extension and a longitudinal (y) extension; the pad being symmetric about a longitudinal center line and the medical dressing comprising a first lobed portion on one side of the longitudinal center line and a second lobed portion on the other side of the longitudinal center line.

3. The medical dressing configured to be applied on intact skin and configured to prevent an onset of a pressure ulcer during use according to claim 2, wherein an anisotropic layer is arranged such that a first direction (x) of the anisotropic layer corresponds to the lateral (x) extension of the dressing, and a second direction (y) of the anisotropic layer corresponds to the longitudinal extension of the dressing, wherein the anisotropic layer is arranged between the gel pad and the adhesive body contact layer.

4. The medical dressing configured to be applied on intact skin and configured to prevent an onset of a pressure ulcer during use according to claim 2, wherein the medical dressing is divided into three separate zones along the longitudinal (y) extension of the medical dressing: one central zone and two lateral zones, wherein the gel pad in at least the central zone comprises a plurality of indentations.

5. The medical dressing configured to be applied on intact skin and configured to prevent an onset of a pressure ulcer during use according to claim 2, wherein the medical dressing is divided into three separate zones along the longitudinal (y) extension of the dressing: one central zone and two lateral zones, wherein a compressive strength of the gel of the gel pad in the central zone is lower than in the lateral zones.

6. The medical dressing configured to be applied on intact skin and configured to prevent an onset of a pressure ulcer during use according to claim 1, wherein the gel of the gel pad has a compressive strength from 1 to 14 kPa at a strain of 25%, as measured according to the compression test.

7. The medical dressing configured to be applied on intact skin and configured to prevent an onset of a pressure ulcer during use according to claim 1, wherein the gel of the gel pad has a compressive strength of from 5 to 40 kPa at a strain of 50%, as measured according to the compression test.

8. The medical dressing configured to be applied on intact skin and configured to prevent an onset of a pressure ulcer during use according to claim 1, wherein the gel of the gel pad is manufactured by polymerizing:
15-50% by weight of a hydrophilic acrylic monomer;
50-85% by weight of a hydrophilic softening agent;
0.001-0.5% by weight of a crosslinker; and
0.05-0.5% by weight of a polymerization initiator.

9. The medical dressing configured to be applied on intact skin and configured to prevent an onset of a pressure ulcer during use according to claim 1, wherein the gel pad has an opacity of less than 25% as measured by a opacity test.

10. The medical dressing configured to be applied on intact skin and configured to prevent an onset of a pressure ulcer during use according to claim 1, wherein the medical dressing comprises an anisotropic layer having a first direction (x) and a second direction (y), wherein a tensile force at 15% strain of the anisotropic layer is higher in the second direction (y) than in the first direction (x), when measured according to a tensile test, wherein the anisotropic layer is arranged between the gel pad and the adhesive body contact layer.

11. The medical dressing configured to be applied on intact skin and configured to prevent an onset of a pressure ulcer during use according to claim 10, wherein the tensile force at 15% strain of the anisotropic layer in the second direction (y) is at least 6 times higher than in the first direction (x), when measured according to the tensile test.

12. The medical dressing configured to be applied on intact skin and configured to prevent an onset of a pressure ulcer during use according to claim 1, wherein the medical dressing comprises at least one gripping tab.

13. A method comprising:
a) applying the medical dressing configured to be applied on intact skin and configured to prevent an onset of a pressure ulcer during use accordingly to claim 1 to a subject at an area of risk of developing a pressure ulcer, thereby reducing the risk of the development of a pressure ulcer at the area of risk of developing a pressure ulcer.

14. The medical dressing configured to be applied on intact skin and configured to prevent an onset of a pressure ulcer during use according to claim 1, wherein the adhesive body contact layer is perforated.

15. The medical dressing configured to be applied on intact skin and configured to prevent an onset of a pressure ulcer during use according to claim 1, wherein the gel of the gel pad has a water content of less than 15% by weight.

16. The medical dressing configured to be applied on intact skin and configured to prevent an onset of a pressure ulcer during use according to claim 1, wherein the medical dressing consists of the backing layer, the gel pad, and the adhesive body contact layer.

17. The medical dressing configured to be applied on intact skin and configured to prevent an onset of a pressure ulcer during use according to claim 1, wherein the adhesive body contact layer extends beyond the periphery of the gel pad and is coextensive with the backing layer to define the border portion around the contour of the gel pad.

18. The medical dressing configured to be applied on intact skin and configured to prevent an onset of a pressure ulcer during use according to claim 1, wherein the backing layer comprises the second opposing side of the medical dressing.

19. The medical dressing configured to be applied on intact skin and configured to prevent an onset of a pressure ulcer during use according to claim 1, wherein an entire area of the adhesive body contact layer is configured to adhere to the dermal surface during use.

20. The medical dressing configured to be applied on intact skin and configured to prevent an onset of a pressure ulcer during use according to claim 1, wherein the gel pad and the adhesive body contact layer are configured to allow the caregiver to perform the blanching test through the medical dressing of an entire area of the subject covered by the gel pad during use, wherein the adhesive body contact layer is configured to adhere to the dermal surface over the entire area during use.

21. The medical dressing configured to be applied on intact skin and configured to prevent an onset of a pressure ulcer during use according to claim 1, wherein the adhesive body contact layer covers at least 60% of a surface area of the gel pad.

* * * * *